US005763166A

United States Patent [19]
Petit et al.

[11] Patent Number: 5,763,166
[45] Date of Patent: Jun. 9, 1998

[54] GENE ASSOCIATED WITH X LINKED KALLMANN SYNDROME AND DIAGNOSTIC APPLICATIONS THEREFROM

[75] Inventors: Christine Petit, Bagneux, France; Jean-Michel Claverie, Rockville, Md.; Jacuqeline Levilliers, Gometz le Chatel, France; Renaud Legouis, Paris, France; Jean-Pierre Hardelin, Paris, France; Georges Lutfalla, Paris, France

[73] Assignees: Institut Pasteur, Paris Cedex, France; The United States of America as represented by the Department of Health and Human Services, Washington, D.C.

[21] Appl. No.: 211,430

[22] PCT Filed: Oct. 9, 1992

[86] PCT No.: PCT/FR92/00956

§ 371 Date: Jun. 30, 1994

§ 102(e) Date: Jun. 30, 1994

[87] PCT Pub. No.: WO93/07267

PCT Pub. Date: Apr. 15, 1993

[30] Foreign Application Priority Data

Oct. 9, 1991 [FR] France .................. 91 12451

[51] Int. Cl.$^6$ ............... C12Q 1/68; C12P 19/34; C07H 21/04; C07K 14/435
[52] U.S. Cl. ............... 435/6; 435/7.1; 435/91.2; 435/320.1; 530/300; 530/350; 530/388.1; 536/23.5; 536/24.31; 536/24.33
[58] Field of Search .............. 435/6, 91.2, 320.1, 435/7.1; 536/23.5, 24.31, 24.33; 530/350, 300, 388.1

[56] References Cited

PUBLICATIONS

Legouis et al., *Cell* 67, 423–435 (1991 Oct. 18).
Franco et al., *Nature* 353, 529–538 (1991 Oct. 10).
Hardelin et al., *PNAS* 89, 8190–8194 (1992 Sep.).
Petit et al., *PNAS* 87, 3680–3684 (1990).
Meitinger et al., *Am. J. Hum. Genet.* 47, 664–669 (1990).
Legouis et al., *Cytogenet. Cell Genet.* 58 (1–4) Abstract #2074 (1991).
Challoner et al., *Nucleic Acids Res.* 14(15), 6299–6311 (1986).
Ballabio, *Am. J. Hum. Genet.* 49(4)(Suppl.), Abstract #55 (1991).
Franco et al., *Am. J. Hum. Genet.* 49(4)(Suppl.), Abstract #2294 (1991).
Incerti et al., *Am. J. Hum. Genet.* 49(4)(Suppl.), Abstract #2307 (1991).

*Primary Examiner*—Kenneth R. Horlick
*Attorney, Agent, or Firm*—Oblon, Spivak, McClelland, Maier & Neustadt, P.C.

[57] ABSTRACT

The invention relates to a fragment of nucleic acid characterized in that it comprises a nucleotide sequence selected from: (A) the sequence SEQ ID No. 1; (B) the sequences of one or more bases; (C) fragments of the said sequences (A) and (B); (D) sequences complementary to the said sequences (A), (B), and (C); and (E) the sequences which hybridize with the sequences (A),(B), and (C). The corresponding peptide sequences are also disclosed. A nucleic acid fragment of the invention may be used as a primer or probe, particularly in a method for diagnosing a genetic anomaly linked to the Kallmann syndrome.

16 Claims, 10 Drawing Sheets

```
  1   GTCGGCGAGGAGGGT CCGGCCGGAGTTGAA GGATTGAACTTTCCC GCTCAGTCGCGGCGG
 61   CTGCCTGGTCCTCAG CAGTGCAGCCCCGGC GCGGAGCAGGGAGCC TCGGCCCGCGCCCGG
121   CGCCCTCGCCCTCGC CCTCGACCCGCAGCC ATGGTGCCCGGGGTG CCCGGCGCGGTCCTG
  1                                    M  V  P  G  V   P  G  A  V  L

181   ACCCTCTGCCTCTGG CTGGCGGCCTCCAGC GGCTGCCTGGCGGCC GGCCCCGGCGCGGCT
 11    T  L  C  L  W   L  A  A  S  S   G  C  L  A  A   G  P  G  A  A

241   GCTGCGCGGCGGCTG GACGAGTCGCTGTCT GCCGGGAGCGTCCAG CGCGCTCCGTGCGCC
 31    A  A  R  R  L   D  E  S  L  S   A  G  S  V  Q   R  A  P  C  A 1  2
301   TCCAGGTGCCTGAGC CTGCAGATCACTCGC ATCTCCGCCTTCTTC CAGCACTTCCAGAAC
 51    S  R  C  L  S   L  Q  I  T  R   I  S  A  F  F   Q  H  F  Q  N 2  3
361   AATGGTTCCCTGGTT TGGTGCCAGAATCAC AAGCAATGTTCTAAG TGCCTGGAGCCCTGC
 71    N  G  S  L  V   W  C  Q  N  H   K  Q  C  S  K   C  L  E  P  C 3  4
421   AAGGAATCAGGGGAC CTGAGGAAACACCAG TGCCAAAGCTTTTGT GAGCCTCTCTTCCCC
 91    K  E  S  G  D   L  R  K  H  Q   C  Q  S  F  C   E  P  L  F  F

481   AAGAAGAGCTACGAA TGCTTGACCAGCTGT GAGTTCCTCAAATAC ATCCTGTTGGTGAAG
111    K  K  S  Y  E   C  L  T  S  C   E  F  L  K  Y   I  L  L  V  K

541   CAGGGGGACTGTCCG GCTCCTGAGAAAGCC AGTGGATTTGCGGCC GCCTGTGTTGAAAGC
131    Q  G  D  C  P   A  P  E  K  A   S  G  F  A  A   A  C  V  E  S

601   TGCGAAGTTGACAAT GAGTGCTCTGGGGTG AAGAAATGTTGTTCC AATGGGTGTGGACAC
151    C  E  V  D  N   E  C  S  G  V   K  K  C  C  S   N  G  C  G  H 4  5
661   ACCTGTCAAGTACCC AAGACTCTGTACAAA GGTGTCCCCCTGAAG CCCAGAAAAGAGTTA
171    T  C  Q  V  P   K  T  L  Y  K   G  V  P  L  K   P  R  K  E  L

721   CGATTTACAGAACTG CAGTCTGGACAGCTG GAGGTTAAGTGGTCC TCGAAATTCAATATT
191    R  F  T  E  L   Q  S  G  Q  L   E  V  K  W  S   S  K  F  N  I
```

FIG.6A

```
781   TCTATTGAGCCTGTG ATCTATGTGGTACAA AGAAGATGGAATTAT GGATCCATCCTAGC
211     S  I  E  P  V   I  Y  V  V  Q   R  R  W  N  Y   G  I  H  P  S 5 6
841   GAAGATGACGCCACT CACTGGCAGACAGTG GCCCAGACCACAGAC GAGCGAGTTCAACTG
231     E  D  D  A  T   H  W  Q  T  V   A  Q  T  T  D   E  R  V  Q  L

901   ACTGACATAAGACCC AGCCGATGGTACCAG TTTCGAGTGGCTGCT GTGAATGTGCATGGA
251     T  D  I  R  P   S  R  W  Y  Q   F  R  V  A  A   V  N  V  H  G 6 7
961   ACTCGAGGCTTCACT GCCCCCAGCAAACAC TTCCGTTCTTCCAAA GATCCATCTGCCCCA
271     T  R  G  F  T   A  P  S  K  H   F  R  S  S  K   D  P  S  A  P

1021  CCAGCACCGGCTAAC CTCCGGCTGGCCAAC TCCACCGTCAACAGT GATGGGAGTGTGACC
291     P  A  P  A  N   L  R  L  A  N   S  T  V  N  S   D  G  S  V  T

1081  GTCACTATAGTTTGG GATCTCCCCGAGGAG CCGGACATCCCTGTG CATCATTACAAGGTC
311     V  T  I  V  W   D  L  P  E  E   P  D  I  P  V   H  H  Y  K  V

1141  TTTTGGAGCTGGATG GTCAGCAGTAAGTCT CTTGTCCCAACAAAG AAGAAGCGGAGAAAG
331     F  W  S  W  M   V  S  S  K  S   L  V  P  T  K   K  K  R  R  K 7 8
1201  ACTACGGATGGTTTT CAAAATTCTGTGATC CTGGAGAAACTCCAG CCAGACTGTGACTAT
351     T  T  D  G  F   Q  N  S  V  I   L  E  K  L  Q   P  D  C  D  Y

1261  GTTGTGGAATTGCAA GCCATAACGTACTGG GGACAGACACGGCTG AAGAGTGCAAAGGTG
371     V  V  E  L  Q   A  I  T  Y  W   G  Q  T  R  L   K  S  A  K  V 8 9
1321  TCCCTTCACTTCACA TCGACACATGCAACC AACAACAAAGAACAG CTTGTGAAAACTAGA
391     S  L  H  F  T   S  T  H  A  T   N  N  K  E  Q   L  V  K  T  R

1381  AAAGGTGGAATTCAA ACACAACTCCCTTTT CAAAGACGACGACCC ACTCGCCCGCTGGAA
411     K  G  G  I  Q   T  Q  L  P  F   Q  R  R  R  P   T  R  P  L  E

1441  GTCGGAGCTCCCTTC TATCAGGATGGCCAA CTGCAAGTTAAAGTC TACTGGAAGAAGACA
431     V  G  A  P  F   Y  Q  D  G  Q   L  Q  V  K  Y   W  K  K  T
```

FIG.6B

```
           9  10
1501   GAAGATCCCACTGTC AACCGATATCATGTG CGGTGGTTTCCTGAA GCGTGTGCCCACAAC
 451    E  D  P  T  V   N  R  Y  H  V   R  W  F  P  E   A  C  A  H  N 10 11
1561   AGAACAACCCGATCA GAGGCATCATCTGGC ATGACCCACGAAAAT TACATAATTCTTCAA
 471    R  T  T  G  S   E  A  S  S  G   M  T  H  E  N   Y  I  I  L  Q

1621   GATCTGTCATTTTCC TGCAAGTATAAGGTG ACTGTCCAACCAATA CGGCCAAAAAGTCAC
 491    D  L  S  F  S   C  K  Y  K  V   T  V  Q  P  I   R  P  K  S  H

1681   TCCAAGGCAGAAGCT GTTTTCTTCACTACT CCACCATGCTCTGCT CTTAAGGGGAAGAGC
 511    S  K  A  E  A   V  F  F  T  T   P  P  C  S  A   L  K  G  K  S 11 12
1741   CACAAGCCTATTGGC TGCCTGGGCGAAGCA GGTCATGTTCTTTCT AAGGTGCTAGCTAAG
 531    H  K  P  I  G   C  L  G  E  A   G  H  V  L  S   K  V  L  A  K

1801   CCTGAGAACCTTTCT GCTTCATTCATCGTC CAGGATGTGAACATC ACCGGTCACTTTTCT
 551    P  E  N  L  S   A  S  F  I  V   Q  D  V  N  I   T  G  H  F  S

1861   TGGAAGATGGCCAAG GCCAATCTCTATCAG CCCATGACTGGGTTT CAAGTGACTTGGGCT
 571    W  K  M  A  K   A  N  L  Y  Q   P  M  T  G  F   Q  V  T  W  A

1921   GAGGTCACTACGGAA AGCAGACAGAACAGC CTACCCAACAGCATT ATTTCACAGTCCCAG
 591    E  V  T  T  E   S  R  Q  N  S   L  P  N  S  I   I  S  Q  S  Q 12 13
1981   ATTCTGCCTTCGGAT CATTATGTCCTAACA GTGCCCAATCTGAGA CCATCTACTCTTTAC
 611    I  L  F  S  D   H  Y  V  L  T   V  P  N  L  R   P  S  T  L  Y

2041   CGACTGGAAGTGCAA GTGCTGACCCCAGGA GGGGAGGGGCCGGCC ACCATCAAGACGTTC
 631    R  L  E  V  Q   V  L  T  P  G   G  E  G  P  A   T  I  K  T  F 13 14
2101   CGGACGCCGGAGCTC CCACCCTCTTCAGCA CACAGATCTCATCTT AAGCATCGTCATCCA
 651    R  T  P  E  L   P  P  S  S  A   H  R  S  H  L   K  H  R  H  P
```

FIG.6C

```
2161  CATCATTACAAGCCT TCTCCAGAAAGATAC TAAACTGTTCAAAAA GATTTTGTGAAATTG
671     H  H  Y  K  P   S  P  E  R  Y
2221  CACAGATGTGTAAGC TTGTTGAACTTCGGC CACGAGACATGCACA CTTCCAGAGGCAGTG
2281  GGAACTGCTCAGAGG CCCGGACTCTCCTAT GTGACTTTAGTGCAG GAAGAACTTCTGTCA
2341  ATCATGGACGCATCT GGAGACAAGTGAGAA ACAGTAGATTGGTGA AGACAGACACCAGTT
2401  CCCTACAAGCATGGA GAAAATGAAGAATAG GCCTGTTTAATGCTA AATTTTGTTTTCATG
2461  TATGGTGTCCCTCAT TTCTATTGAATTACA ACAGAACTCAGTTTT CCCTGAATTTGGAGC
2521  ACCAAACTCCGCCCC AAAAAGGAGAGTAAC AAATACACAATTCAC ACATAACACTAAGCG
2581  TAAATCTAATCAATA AAATATATTTTTGAC TAAATTATTGATTCG ATATGAAAAATCAAC
2641  TAAGATTACACAGCT TTGTTTTTTTGAATC TTTCCTAAGATCATT TTTATCCTAGGTGAT
2701  TTTTAAATGAAAATG TGTAATCTAAAATAT ACCAGCGAATTTAAA TCTAAAAATGCTCCT
2761  ACTTTAAGTACCTTG TGCTGCTCTTTATGC AAAGGTAAATCAAAG TTCCCTCTATAAATT
2821  ATGATTTACAAAAGA CACCCAAGCCAGAGG AACTCAATGAAATAA GCTGCTAATCAGATT
2881  TTACCTTGGAGAAAT GAAAATTATTCTTG GGGATGCCTTTTAAT ATTTGATCCTATTAT
2941  GTGAGAGATTTTCCT GATATGTTATCTTAT TTATATTTTCCCTTA TTTTCCTCAATGCAG
3001  ATAATAGCTTTTGGT GCACTTTTGTTTCAC CATCTGAAAATTCAC AAAACTTCTTGCTTC
3061  AAATGAAAAAATCCC AACTATTGAGCATGT TTAAATCTTTGCAGA GATTTGCCTTTTCTT
3121  AATCAAAGAAAGGTC TTTGTGTGCTAGAAT ATTATTGGTAATGTT TTAAAAATTCCTTTG
3181  ATTGATAGAGAAGGA CAGTTATTTGCATTT AATTCACCCATATGC TTTCAAATCTAGTAT
3241  ATCTTACTTTTTGGA AATGTTTTATGCTAC AAATTAGTGCCTTGT AGCATGAACTTAAGT
3301  CAAAACGTGTTATCA ATATAGAGTGTTGCA GTGTATATTGTAACA ACCTAAAACGCAGAG
3361  AAGTTTAATTTAATA CTGTTTTTTTTCTTG AAGGAATACTCACAT ACATGGTTTGAAATG
3421  TGCATAGATATGCAT GTCTATATAATTATA AATGCATGTGTATAT ATATGCAAATATATG
3481  TACATATACATGTAT ATACACACAGACACA TGCATATACATGAAT ATACCTTGAGCATGA
3541  ATCCCTGGAGAAATC GTTTTCCTAGGCTCA CCAATGGTGAGTAAA GATACAGCTCTTTTA
3601  AAGGTCATAAGGATA ATATATTTTCCCCAT CAATGCTGATTCTGA GAAAAGAGCAATTTA
3661  TCAAAATTAAACACT GTAAAAGAAAGGTGT CCATATGTCTTTACC TACCTAAGTAAAACA
3721  GGAAGAAAATCAGTA ACATTATCCTTAGGT TTTGACAATGGTACT TGCTTCTTGTTGTTT
3781  TATTGTTTCCTGAAT TCATGCAGATGCCTG GCCATTCCTGGGAAG AGTGGATAACTCAGA
3841  AGTCACTGTACTCCA CAGAGCCTCACTGCA GTGTCTAAAGGTAGA TGCAAATTAAAATGC
3901  AGGGAAAATAACTTT TCTGATGTTGATGCA TGTCTTTGGGAAACA CATTTATAAACATGG
3961  ATACCTGATAATAGA TATTGAAACCCATTT CCTGTGTGTTAAAAT ATTTAAAAAGTGGAT
4021  ATTCCAGGAATGTTT TGCAGCTTTGTACAA GTAACATAAATTGGA CACCTCAGAATGAAA
4081  GTTCATGTTGGTTCT GAATGGTTCACTGCA GCTCCTGTCACAAGC TGGGATGGATTTATC
4141  ACATTGAGTTATGAA ATTACCTGGTTCTAA GAATTTTTGACTGGC AAAAATAGAAAACAA
4201  TCTTCATTTGAAAAC ATCCCTAAGCTTGAA TAAATGGATACCATA GATAGCTTCTCTTTT
4261  TTATTCTGGTGTCAT TACCAGCATCTGAAT TCAAGTTCTTAAAA TTTCAAAAATTAAAA
4321  TTTTTCATTATTAGC TATCCATTTATCTTT TACATGAACTTGTCA TGAACAAATTCAAAT
4381  GTTATGCCAGCAAA TTTTTGTACTGTTGC ATAGTTAAAAATGCT GGGAGTCTCTGCATA
4441  GATACAAAATATTAT TAAATTATTACATAA ATTTAATTTTATAAA ATTTAATCATGCTTC
4501  TTTTGTCTGGTAATA GACATTGGACAGATA TTTTTAGTTCAGATG GTGATTCTGAAGCTT
4561  ACATCTCCCTTAAAA AAATCTAAAGCAGCT CTTATGGGCTTCTAA TTTTAATATAAATAA
4621  ATAATTTAAATTTTA TTGGTGTTATTGGAA GAAAAATGCTATTAA TGGGCTAATAAAAAA
```

FIG.6D

```
4681  CATGTGTTTCTCTTA TGGATTTTAATAAGC TCCAGTATTATTCAA ATGATCAAAAATATA
4741  GTTATAATTTTTTGA ATTTTAAAAATGTGA TTGCTCTAATAAAGA ATAAAATCTATGCTT
4801  TTTAACAAACATAGT TTTGGTGCCTAATTC TGTAATATGTTTTAT TGAAATTAGATTCAT
4861  TTCTCTAATGTGAGA AAAATATATCCAGTA ATAGTATTGACTGTT TAAAAAAATTGAGCTC
4921  ATCAAAAATATTGTC ATCAAATACAGGTGG TTAATCTGACATACA TTGCAGTTACATGCA
4981  TTATTTTATTTACA ACATTTGCTCCTTAA TGATGAATTTATCTG TGTTACCCTGTTTTT
5041  CTACCTGGAACTCCA TAGAATGATGTTTGC AAACCAACATGTGCT CTTTTCAGTCATTCA
5101  CTGTTTTAATATGAC ATGGTAGAGAAGATA ACGTTTATGGCAGGT AATTTTTTGTAATGT
5161  GTATTAAACGAAGTT CAAAGATTAGAAATA CATCTGTGTCCTGAA AACCTTAGATACATA
5221  GCCGACTGTATACAG AGGTTCATCTCAACC TCAACACTATTGACT TTTGGGGCTGGATAG
5281  TTCTCTGTTGTGGGG GTTTGTCTTGTGCAC TGTAGGTTTTTAGTA GCATCCACACTTTCT
5341  CCTCACCAGATGCCA GTTGCACCCTCCCCC AAGTTGAGACAACCA AAAATGTCTCCAGAT
5401  ATTGCCAGCTACCCC TTGAGGGATGGTACC TCTGGTTGAGAACCA TTGCTAGAGAATGAT
5461  CTTTACTGAATTTGC CCTTTATAAGAAACC CAGTGAATTTCTAGA GCAAGTCCCAAAAAC
5521  TAAGGGACAGCTAAG AAGTTATTATGGTTG ACTTCAAAGGCCTAA ACTGTGTTTTTTATG
5581  TCCACTAAACAACTT GATTAAAAGACGGAA TTTTGACTCGTGTCT GTATCATACAAGTAC
5641  AAATACTAATTTTGC CCTATGTATCCGTAA ATGTCATTTGTGATT TTGACTTATTTATTT
5701  AATGCCCTTTCTTAT GCCGTGGGTTTTCAA GTTACTCATTTCTA TGGTTGCAAATAACT
5761  CTAAAACTTATTATA TAAACTTTCATATTA TAGGCAGAACACAAT GGCTAAATATCTGTT
5821  GCATGTACTTTAAAG TTTATTATAAAATAT AAACAGATATATAAA GATGTTGACTCTTAC
5881  CTGTGATTTGCATG GTCAGACTCGGTGTC AGGTACGGAGAGGAT TCTCATGACTGTCTT
5941  ACCTCTACTGAATAT TCTAGTGAGTTATAT GATTTACGGAGTGAT TAACAGAGGTCTATA
6001  TAAAGTTACTTTTCC CCTTTACTTAATTAT ATTGTAGTGTGCAGA TAACAAAACTGCTAC
6061  CTTCTCATCCAAGTG GTCTGTAGAATTCAT GTCCCTTACAGTGGT CATTTAAAGTCAATA
6121  TTTATTTATGTATGT AATAAAAAAAGTTGG ATTTTTGTGTATGTC TGTCACATTATTTAG
6181  AGACAAGTAATCTTG TAAAAATGTTTTGTA AAAAACAAAAAAGTA TTGTAAATAGTCTTG
6241  ATATTCTGTGACTCA TTATTTTCATGTTAG AGTTTGTACATACTG GTTCAATAATAAAGT
6301  ATCCTTAAACCAGA
```

FIG.6E

GENE ASSOCIATED WITH X LINKED KALLMANN SYNDROME AND DIAGNOSTIC APPLICATIONS THEREFROM

BACKGROUND OF THE INVENTION

1. Field of the Invention

The subject of the present invention is a nucleotide sequence of the gene associated with the X chromosome-linked Kallmann syndrome, the applications of this sequence or of fragments of this sequence as nucleotide probes or nucleotide primers for the specific amplification of the gene or of fragments of the gene associated with the X chromosome-linked Kallmann syndrome, as well as all or part of the peptide sequences derived from the nucleotide sequence and their applications.

2. Discussion of the Background

Kallmann syndrome is characterized by the association of a hypogonadotropic hypogonadism with anosmia. This syndrome is also called olfactogenital dysplasia because of the existence of cases where an agenesis of the olfactory bulbs exists.

There are several modes of transmission of the syndrome: a mode of transmission linked to the X chromosome, a recessive autosomal mode and a dominant autosomal mode. The incidence of Kallmann syndrome has been estimated at one male in 10,000. The excess by a factor of 6 to 7 of the number of representatives of the male sex who are carriers of the syndrome compared with the number of representatives of the female sex suggests that the form linked to the X chromosome is the most frequent. In this form, individuals of the female sex can be affected by hyposmia.

The association of the two symptoms remained for a long time enigmatic. However, recent studies have reported a common route for the development of the olfactory neurons and the neurons which synthesize the gonadotrophin-releasing hormone (GnRH).

The origin of both types of neuron is in an olfactory placode.

The central extensions of the olfactory neurons go across the ethmoid up to the inferior face of the forebrain. A contact between the ingrowing olfactory nerves and the forebrain is necessary for the development of the olfactory bulbs. The GnRH-synthesizing neurons also migrate towards the brain, go across the ethmoid bone with the branches of the nervus terminalis.

Finally, they reach the septal preoptic aera and the hypothalamus. This suggests the implication of the Kallmann gene (KAL) in this common embryonic development.

The discovery by Schwanzel-Fukuda et al., 1989 (23) that the GnRH-synthesizing neurons were present only outside the cerebral tissue in a human foetus having an X-linked Kallmann syndrome reinforces this hypothesis.

Genetic linkage analyses and deletion studies have permitted the location of the X-linked KAL gene in the vicinity of the STS (steroid sulphatase) locus in the Xp 22.3 region (Ballabio et al. (6) and (7)).

Analyses of DNA from two individuals having terminal Xp deletions, one having a Kallmann syndrome and not the other, permitted the authors of the present invention to site at least a part of the gene in an interval spanning less than 350 kb (KAL interval) (Petit et al. (20)). This interval is located between 8.6 and 8.95 Mb from the Xp telomere.

SUMMARY OF THE INVENTION

The present inventors have now isolated and sequenced the complementary DNA corresponding to the gene associated with the X chromosome-linked Kallmann syndrome. Starting with a patient LIL 155 having a terminal deletion on the short arm of the X chromosome (Petit et al. (20)) and with a patient AM having a translocation Xp 22.3, Yq 11 (Tiepolo et al., (26)), it was possible to carry out a precise determination of the size of the KAL interval and to sequence the entire interval.

The coding exons of this interval have been searched out. Among 19 potential exons, two proved to be conserved in various animal species.

One of the two was used to isolate cDNA clones obtained from foetal banks.

From the cDNA sequence, the inventors were able to deduce an extracellular protein of 680 amino acids, containing a whey acidic protein (WAP)-type motif whereas another region of the protein exhibits significant homologies with adhesion molecules.

Because of the homology with adhesion molecules, the inventors called the gene associated with the X chromosome-linked Kallmann syndrome ADMLX gene.

The ADMLX gene has 14 exons, designated below by the numbers I to XIV.

DETAILED DESCRIPTION OF THE PREFERRED EMBODIMENT

The subject of the present invention is thus a nucleic acid fragment, characterized in that it has a nucleotide sequence chosen from:

(A) the sequence SEQ ID No. 1,
(B) the sequences differing from the latter by mutation, insertion, deletion or substitution of one or more bases,
(C) fragments of the said sequences (A) and (B),
(D) the sequences complementary to the said sequences (A), (B) and (C), and
(E) the sequences which hybridize with one of the sequences (A), (B), (C) or (D).

The subject of the present invention is also a cloning vector containing a nucleic acid fragment as defined above.

A preferred cloning vector is the plasmid p85B containing a cDNA having the sequence SEQ ID No. 1 as defined above, deposited at the CNCM (Collection Nationale de Cultures de Microorganismes) on 26 Sep. 1991 under the No. I-1146.

The subject of the present invention is also a pair of oligonucleotides capable of acting as primers in the specific amplification of the gene or of fragments of the gene associated with the X chromosome-linked Kallmann syndrome in a biological sample, characterized in that it consists of two nucleotide sequences chosen from (A), (B), (C) and (D), with the proviso that one of the members of the pair (D), consists of a sequence belonging to (D).

The primers preferably have a length of 18 to 30 nucleotides and, preferably, of 18 to 22 nucleotides.

One of the two primers is complementary to the (+) strand of the template and the other primer is complementary to the (−) strand. It is important that these primers do not possess a secondary structure or a mutually complementary sequence. Furthermore, the length and the sequence of each primer should be chosen in such a manner that the primers do not hybridize with other nucleic acids present in the biological sample.

The amplimers selected as specific primers for the amplification of nucleotide sequences can be chosen for example by following the method described by Griffai et al. (30).

Advantageously, the primers can also consist of oligonucleotides of 18 to 30 nucleotides, preferably 21 to 25, chosen from the intervening sequences flanking the exons. They consist especially of the pairs having the following nucleotide sequences.

SEQ ID No. 3 and SEQ ID No. 4, for the non-coding 5' part of Exon I;

SEQ ID No. 5 and SEQ ID No. 6, for the coding part of Exon I;

SEQ ID No. 7 and SEQ ID No. 8, for Exon II;

SEQ ID No. 9 and SEQ ID No. 10, for Exon III;

SEQ ID No. 11 and SEQ ID No. 12, for Exon IV;

SEQ ID No. 13 and SEQ ID No. 14, for Exon V,

SEQ ID No. 15 and SEQ ID No. 16, for Exon VI;

SEQ ID No. 17 and SEQ ID No. 18, for Exon VII;

SEQ ID No. 19 and SEQ ID No. 20, for Exon VIII;

SEQ ID No. 21 and SEQ ID No. 22, for Exon IX;

SEQ ID No. 23 and SEQ ID No. 24, for Exon X;

SEQ ID No. 25 and SEQ ID No. 26, for Exon XI;

SEQ ID No. 27 and SEQ ID No. 28, for Exon XII;

SEQ ID No. 29 and SEQ ID No. 30, for Exon XIII;

SEQ ID No. 31 and SEQ ID No. 32, for Exon XIV.

The PCR amplification conditions are advantageously the following: 30 cycles of:

denaturation at 94° C. for 1 minute, annealing at 55° C. for 1 minute, extension at 72° C. for 1 minute, except for the pair SEQ ID No. 3 and SEQ ID No. 4, where the annealing takes place at 58° C. in the presence of 10% DMSO (V/V), the pair SEQ ID No. 5 and SEQ ID No. 6, where the annealing takes place at 63° C. in the presence of 10% DMSO (V/V) and the pair SEQ ID No. 23 and SEQ ID No. 24, where the annealing takes place at 55° C. in the presence of 10% DMSO (V/V).

The amplified fragments can be identified after an agarose or polyacrylamide gel electrophoresis or after a capilliary electrophoresis or alternatively after a chromatographic technique (gel filtration, hydrophobic or ion-exchange chromatography). The specificity of the amplification can be controlled by molecular hybridization using as probes the sequences (A), (B), (C), (D) or (E), plasmids containing these sequences or amplification products. These probes may be labelled or otherwise by radioactive elements or by non-radioactive molecules.

The subject of the present invention is also a nucleotide probe specific for the gene associated with the X chromosome-linked Kallmann syndrome, characterized in that it contains at least 20 consecutive nucleotides chosen from the nucleotide sequences (A), (B), (C), (D) and (E) as defined above.

The non-labelled sequences can be used directly as probes, however, the nucleic acid sequences are generally labelled with a radioactive element ($^{32}P$, $^{35}S$, $^{3}H$, $^{125}I$) or with a non-radioactive molecule (biotin, acetylaminofluorene, digoxigenin, 5-bromodeoxyuridine) in order to obtain probes which can be used for numerous applications. In this latter case, it will be possible to use one of the labelling methods described in FR 2,422,956 and FR 2,518,755.

The hybridization technique can be performed in various ways (Matthews et al. (28)). The most general method consists in immobilizing the DNA from the biological sample on a support (nitrocellulose, nylon, polystyrene and the like) and in incubating, under well defined conditions, the immobilized target DNA with the probe DNA. After hybridization, the excess probe is removed and the hybrid molecules formed are detected by the appropriate method (measurement of the radioactivity, of the fluorescence or of the enzymatic activity linked to the probe and the like).

When a sufficient quantity of DNA can be extracted from samples to be analysed, the sequences described above can be used to detect and identify the gene or a fragment of gene associated with the Kallmann syndrome directly in these samples. In the opposite case, a rapid culture in liquid medium can be performed before extraction of the DNA, or, alternatively, the small quantity of DNA extracted from the sample can be subjected to the PCR technique.

The subject of the present invention is also a method of detection of a genetic abnormality linked to the Kallmann syndrome in a biological sample containing human DNA comprising the following steps:

a) bringing the biological sample containing the DNA into contact with a pair of specific primers as defined above, the human DNA contained in the sample having been optionally rendered accessible to hybridization and under conditions permitting a hybridization of the primers with the human DNA contained in the biological sample;

b) amplification of the human DNA;

c) revealing the amplification products by appropriate techniques;

d) optionally detecting a mutation or a deletion by appropriate techniques.

The mutations can be detected by the technique of single-strand conformation polymorphism (SSCP) analysis as described by M. Orita et al. (29), or by that of denaturing gradient gel electrophoresis (DGGE) such as that described by R. Myers et al. (30).

The deletions can be detected by determination of the length of the amplified fragments, for example by a polyacrylamide gel electrophoresis or alternatively by determination of the sequence of the amplified fragment.

The method of detection of a genetic abnormality linked to the Kallmann syndrome can be performed for example on a sample containing cells of human foetus, after culturing the said cells.

The subject of the present invention is also a kit for the detection of a genetic abnormality linked to the Kallmann syndrome in a biological sample, comprising the following elements:

a pair of specific primers as defined above, the reagents necessary for carrying out a DNA amplification, a component which makes it possible to determine the length of the amplified fragments or to detect a mutation.

The subject of the present invention is also a peptide sequence characterized in that it is encoded by one of the nucleotide sequences (A), (B), (C) or (E).

Its subject is more particularly a peptide sequence characterized in that it contains a sequence chosen from:

(A) the peptide sequence SEQ ID No. 2, (B) the peptide sequence between $C_{22}$ and $Y_{680}$ of the sequence SEQ ID No. 2, (C) fragments of the sequences (A) or (B), (D) the peptide sequences which differ from the sequences (A), (B) or (C) by insertion, deletion or substitution of one or more amino acids and which possess the same activity.

The subject of the present invention is also monoclonal antibodies directed against a protein or a peptide having a peptide sequence as defined above.

The subject of the present invention is finally a process for assaying a protein or a peptide having a peptide sequence as defined above using the monoclonal antibodies according to the invention.

The subject of the invention is in addition a therapeutic method for the Kallmann syndrome in a human patient consisting in transferring into somatic or germ cells of the said patient all or part of a nucleic fragment chosen from the sequences (A), (B), (C), (D) and (E).

The cDNA sequence (SEQ ID No. 1) was obtained by the following steps:

(I)—Isolation of a clone containing all the constitutive DNA of the KAL interval from a YAC (Yeast artificial chromosomes) library: clone YAC 376 B4, (II)—Characterization of the KAL interval by carrying out a subcloning of the YAC 376 B4 clone followed by an analysis by differential hybridizations, (III)—Search for open reading frames in the KAL interval which made it possible to detect two exons belonging to the ADMLX gene, (IV)—Screening of human cDNA libraries with a probe (485 S1) derived from one of the exons and isolation of a clone containing the ADMLX gene.

The protein was characterized from the cDNA sequence obtained. Its expression was studied in various tissues.

By comparison with the native gene, it was possible to characterize genetic abnormalities in various patients having a Kallmann syndrome.

BRIEF DESCRIPTION OF THE DRAWINGS

In order to understand the invention, reference will be made to the appended figures in which:

FIG. 6 represents the cDNA of the ADMLX gene and the amino acid sequence deduced from the nucleotide sequence.

EXAMPLES

Figure 1:
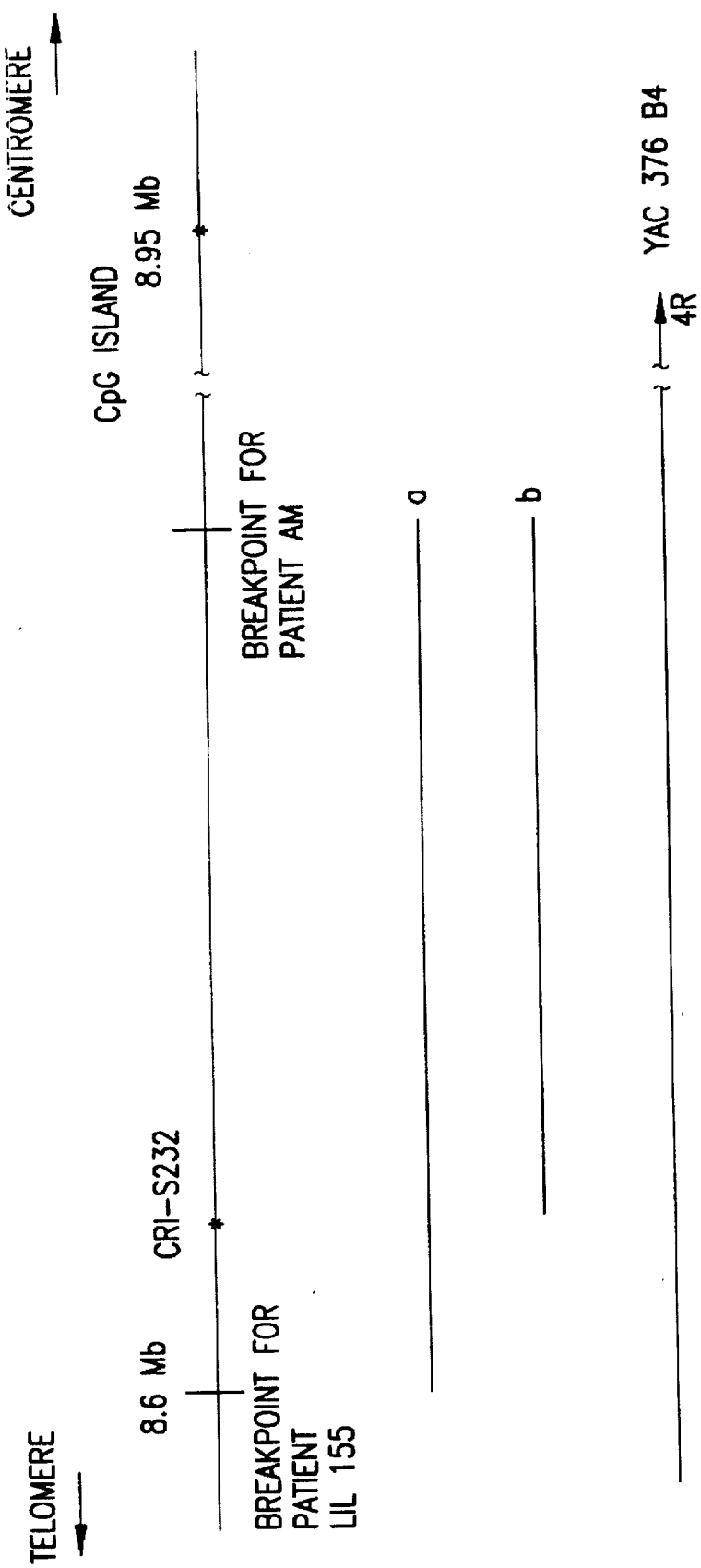
FIG. 1 schematically represents the KAL interval as defined prior to the invention (a) and the KAL interval as defined according to the present invention (b)

The general cloning techniques used within the framework of the present invention are described below:

A—Cell lines

Epstein-Barr virus-transformed lymphoblastoid cells from the patient LIL 155 and fibroblasts obtained from patients AM and FL were cultured in an RMPI 1640 medium (Flow Laboratories) supplemented with 10% foetal calf serum (Jacques Boy, Reims, France).

B—PCR amplification using Alu PCR probes

The PCR (Polymerase Chain Reaction) amplification was performed with 50 ng of YAC DNA clone, 250 mM of primers in 10 mM of tris-HCl buffer (pH 8.3 at 20° C.) containing 50 mM of KCl, 1.5 mM of MgCl$_2$, 0.01% gelatine, dNTPs (dATP, dCTP, dGTP, dTTP) each at a concentration of 100 µM (Pharmacia) and 2.5 units of Taq DNA polymerase (Cetus) (50 µl total volume). An initial denaturation was carried out for 2 min at 94° C., followed by 30 cycles consisting of denaturation at 94° C. (1 min), annealing at 60° C. (1 min) and extension at 72° C. (4 min). The specific primers were obtained from the Alu consensus sequence: primers 278 and TC-65, Nelson et al., 1989 (17) and from the right and left arms of the vector pYAC4: primers 4R and 4L; Nelson et al., 1991 (18).

C—PCR on the cDNA cDNA was synthesized by extension of primers using random hexamers at a concentration of 5 µM (Pharmacia) and 200 units of reverse transcriptase from the Moloney murine leukemia virus (BRL) for 1 µg of total RNA.

1 µg of total RNA was incubated at 42° C. for 30 min in 20 µl of 16.6 mM (NH$_4$)$_2$ SO$_4$, 1.5 mM of MgCl$_2$, 10 mM of β-mercaptoethanol, 6.7 µm of EDTA, 67 mM of tris-HCl (pH 8.8 at 20° C.) containing 20 units of RNasin (Promega) and dNTPs, each at a concentration of 100 µM.

The tubes were heated at 95° C. for 5 min and cooled on ice.

A PCR was performed on the single cDNA strand in the reverse transcription mix supplemented with 10% DMSO (v/v) and dNTP, each at a concentration of 100 µM, in a final volume of 100 µl. The two primers of 21 nucleotides were used at a concentration of 0.3 µm. After 10 min at 80° C., two units of Taq DNA polymerase (Cetus) were added, and mineral oil was deposited at the surface of the solution. An initial denaturation at 94° C. (2 min) was followed by 30 to 40 cycles consisting of denaturation at 94° C. (45 seconds), annealing at 55° C. (1 min) and extension at 72° C. (45 seconds).

D—Southern analyses

Digestions with the restriction enzymes (EcoRI, HindIII, TaqI, PstI) were performed with 10 to 15 enzymatic units per µg of genomic DNA. Digestions of DNAs, migrations and transfers onto membrane were performed as described by Petit et al., 1988 (19). In order to minimize the background noise, the probes obtained by Alu-PCR were hybridized at 65° C. for 6 hours with 1.5 mg per ml of sonicated human placenta DNA, before the hybridization on blot. The membranes were washed at 65° C. in 0.1% SDS, 2× to 0.1×SSC according to the nature of the probe. "Zoo-blots" were prehybridized and hybridized according to the technique described by Howley et al., 1979 (12). The washes were carried out at 42° C. with a solution containing formamide (25 to 35%), 1% SDS, 1M NaCl, 5 mM EDTA and 50 mM of phosphate buffer (pH 7.2).

E—Analyses by pulsed-field gel electrophoresis (PFGE)

The analyses of high-molecular weight DNA were performed on TAFE (Beckman) and OFAGE (LKB Pharmacia) equipment. A reversed field was also used with the "DNAstar-pulse" program. The digestion and electrophoresis conditions are those described by Petit et al., 1988 (19).

F—Subcloning of the clone YAC 376 B4

A partial digestion with MboI was performed on the high-molecular weight DNA obtained from the clone YAC 376 B4. The restriction fragments were ligated into a vector λ EMBL3, after determination of the size (20–40 kb) on a 0.5% agarose gel. The screening in order to characterize the clones containing the human DNA was performed with an Alu probe. The DNAs from 150 positive clones were extracted, (Manfioletti and Schneider 1988; Coulson and Sulston, 1988), and digested with Taq I. The restriction fragments were separated on agarose gel, transferred and hybridized with the total DNA from the clone YAC 376 B4 and with various other probes (Alu, Kpn, polyAC, polyAG, CRI-S232 and probes obtained from Alu-PCR). The overlapping clones were aligned by analysis with a scanner (laser scanner, Molecular Dynamics, Visage 4.3, Bioimage) and by comparison of the restriction patterns by means of a computer program (Bellanné-Chantelot et al., 1991(8)).

G—Sequencing reaction and alignment

The sequencing of the cDNA clones and of the genomic DNA was performed on single-stranded M13 templates. The DNA was sonicated, fractionated (600 to 1200 bp) on agarose gel and the blunt ends were ligated into a vector mp18M13. The single-stranded templates were sequenced with fluorescently tagged M13 primers, using Taq DNA polymerase (NBL) on an Applied Biosystems 310 A sequencer. The raw sequence data were treated using the Staden shotgun package program (Staden, 1987(25)) modified so as to be able to treat this genomic program (750,000 nucleotides sequenced).

H—cDNA libraries

Two human foetal brain cDNA libraries were bought from Stratagene. One in a vector λ Zap II, primed with oligo (dT) and in a random manner, was obtained from a normal woman having undergone a late abortion at 17–18 weeks, the other in Uni-Zap XR, primed with oligo (dT) and in a random manner, was obtained from donors 15 to 20 weeks pregnant.

In addition, a λ library was produced from a 36-day old Macaccus fascicularis foetus. Total RNA was prepared by modifying the hot phenol extraction method (Sambrook et al., 1989 (21)). The ground tissues were lysed in 10 mM sodium acetate (pH 5.2), 0.5% SDS, and then extracted with phenol at 55° C. The poly A (+) RNAs were purified and the synthesis of cDNA was performed using random hexamers in conformity with the recommendations of the manufacturer (Pharmacia). The cDNAs were cloned into a vector λ gt10. One million independent clones were plated and transferred onto nitrocellulose membranes (Hybond C-super, Amersham). The hybridizations and the washes were performed as described above for the Southern analyses.

I—Screening of the exons by multi-criteria automated procedure

The genomic DNA sequence was screened for the candidate exons before the end of the process which leads to the assembly of the various fragments into a single sequence (Contig process). Both orientations of the 67 kb DNA were merged into a single sequence and subjected to a multi-criteria automated process designed for the detection of internal coding exons. This process is based on considerations relating to the open reading frames (ORF), the putative splice junctions, the differences between the nucleotide compositions of hexamers and the segmental similarities with known proteins. All the open reading frames (defined between two successive stop codons) with a minimum length of 50 nucleotides were selected. All the potential exons (even overlapping) inside these open reading frames were in addition delimited starting from all the possible pairs of splice junctions. All the segments having a positive exon potential value (Claverie et al., 1990(10)) were translated into amino acids, and tested for their significant similiarity with known proteins using the BLAST p program (Altschul et al., 1990 (3)) and the optimal PAM 120 scoring matrix (Altschul et al., 1991(2)). The best candidates and the cDNA probes were chosen from considerations based both on similarities of scores and the exon potential index. The best candidate (CS1) corresponded to exon 1993 to 2134 on the sequence SEQ ID No. 1 with an N-CAM L1 similarity.

J—Analysis of the protein sequence

Analysis of the primary structure of the open reading frame of the Kallmann gene was performed using known computer tools and programs such as PC gene. BLAST p and FASTA (Bairoch, 1991 (5), Lipman and Pearson, 1985 (15), Schuler et al., 1991 (22), and Altschul and Lipman, 1990 (4)), and the collection of protein sequences (Boguski et al., 1991 (9)).

Similarity studies were in addition performed by means of conventional computer programs and using known protein sequences.

Figure 2:
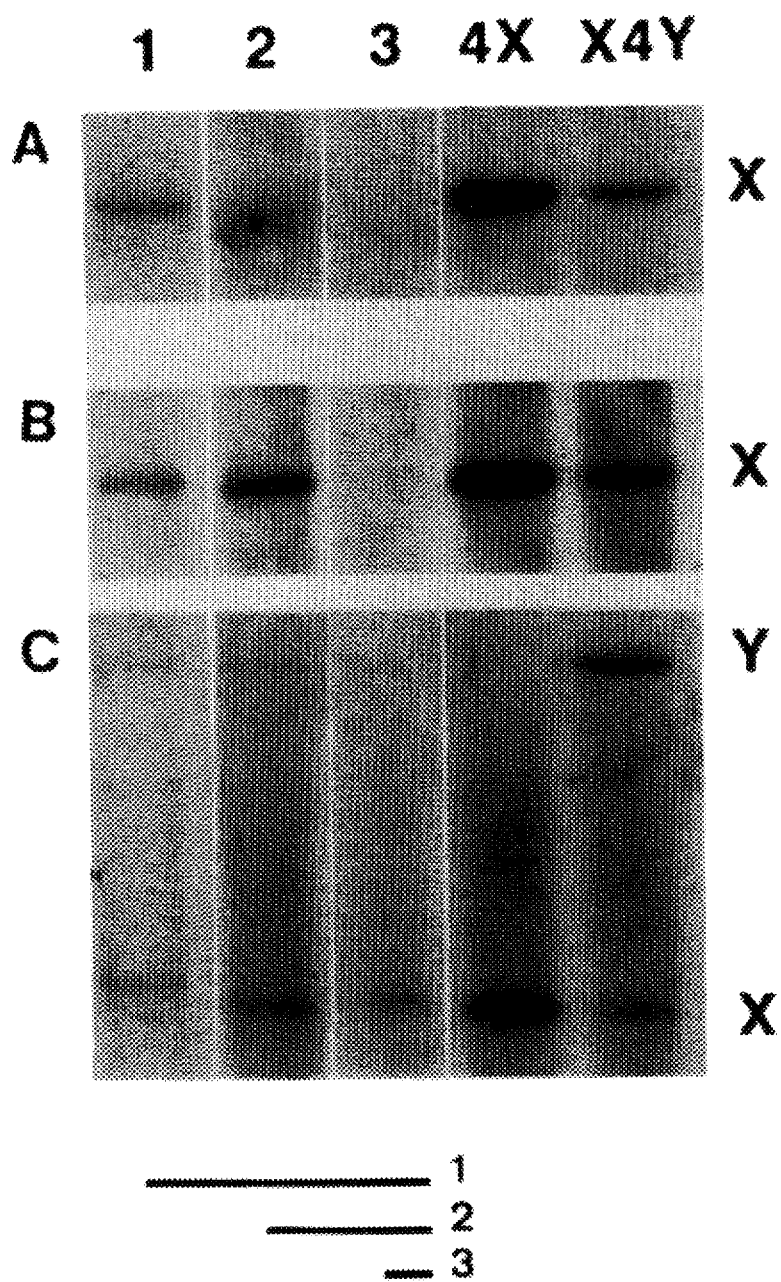
FIG. 2 represents the results of Southern blot analysis of hybridization with probes obtained from the clone YAC 376 B4, the DNAs of patients FL(line 1), LIL 155(line 2) and AM(line 3) all having terminal deletions in the Xp 22.3 interval.

I) Isolation of a clone (clone 376 B4) containing the KAL interval from a library of YACs Using the CRI-S232 probe (Knowlton et al., (13)) described for detecting a locus inside the KAL interval as defined prior to the invention, the inventors isolated 13 YAC clones from the CEPH Mark I YAC library (Albertsen et al., 1990 (1)). Various probes were obtained from these YACs, using PCR amplification with Alu primers (see point B). The PCR amplification products derived from YAC 376 B4 were obtained using the primers 278 (int 2), TC 65 (int 1) and 4R and 278 (4 R376 B4). These probes were hybridized with DNAs previously digested with Taq 1 from a panel of patients all having terminal deletions in the Xp 22.3 interval. The results of Southern analysis are represented in FIG. 2. Among these patients, LIL 155 had a deletion on the short arm of the X chromosome; AM had a translocation Xp 22.3; Yq 11. Only AM had a Kallmann syndrome.

In FIG. 2, the breakpoints for patients 2 and 3 define the KAL interval delimited prior to the invention.

4X and X4Y refer respectively to a patient of female sex having 48 chromosomes of which XXXX and a patient of male sex having 49 chromosomes of which XYYYY.

The probe B (int 1) mapped in the KAL interval whereas the probes A (int 2) and C (4R 376 B4) mapped at the distal and proximal ends respectively.

This has made it possible to define 20 deletion intervals in the 10 Mb terminal segment. The probes were also hybridized with a panel of Yq, which made it possible to define 7 deletion intervals. 12 YAC clones were found to come from the X chromosome and 1 (YAC 218 F9) from the Y chromosome. Only one probe (int 1), obtained from a single 352 kb YAC clone, mapped within the KAL interval. This clone was called 376 B4. Two other probes obtained from the same YAC clone (int 2, int 3) mapped in the deletion interval situated immediately at the distal end of the KAL interval, whereas one probe obtained from the right end (4R-376 B4) mapped in the deletion interval situated immediately at the proximal end (FIG. 2). The clone YAC 376 B4 thus encompasses the KAL interval. Insofar as one deletion comprising all the X loci detected by the probe CRI-S232 has been described as not being associated with the Kallmann syndrome (Ballabio et al., 1990), the interval can be reduced to the distance between the locus detected by the probe CRI-S232 and the breakpoint for the patient AM (FIG. 1). From the distance between the loci detected by the probes CRI-S232 and 4R-376B4 (determined from the physical map of the clone YAC 376 B4), the present inventors concluded that the KAL interval thus redefined did not exceed 125 kb.

II) Characterization of the KAL interval

1—Subcloning of the clone YAC 376B4

The clone YAC 376 B4 was subcloned into a vector λ EMBL3. A map of the fragments assembled into a single sequence (contig map) of 180 kb of the inserts of the λ phage covering the KAL interval was established.

2—Differential hybridizations

Hybridization with the EcoRI fragments obtained from subclones of YAC 376 B4 in λ with the DNAs from normal men and women and from individuals 48, XXXX and 49, XYYYY (so as to identify the X-specific and Y-specific bands by assay) showed a colinearity of the DNAs of the YAC and genomic clone. It also revealed X-Y homologous fragments.

Figure 3:
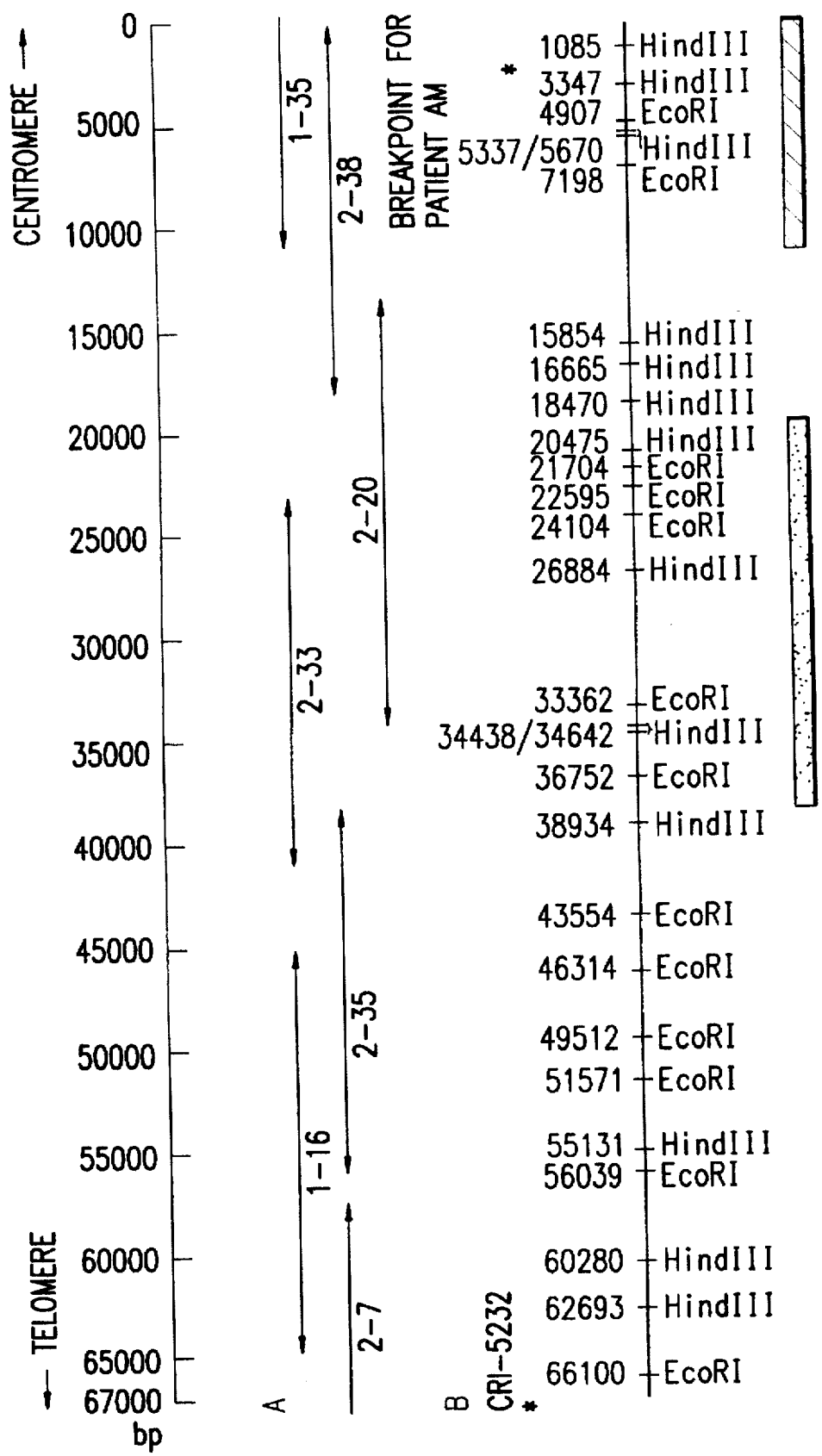
FIG. 3 represents the map of the KAL interval.

In FIG. 3. A) represents the contig map of the recombinant λ subclones obtained from YAC 376 B4 which were sequenced, only the proximal EcoRI fragment of 9 kb of the clone 2–7 was sequenced.

B) represents the restriction sites for EcoRI and HindIII. The breakpoint for the patient AM and the locus detected by the probe CRI-5232 are indicated by asterisks.

C) represents the regions homologous between Xp 22.3 and Xq 11 (shaded bands). These homologies were defined by hybridization of the EcoRI fragments obtained from λ clones with the DNAs from individuals 46, XX, 46, XY, 48, XXXX and 49, XYYYY.

The strongest homology is detected in the centromere portion of the KAL interval (evaluated by the intensity of the hybridization signals).

All these X-Y homologous fragments hybridized with the clone YAC 218 F9 (obtained from the Y chromosome, provided by CEPH (Centre d'Etudes du Polymorphisme Humain)). This homology between Xp 22.3 and Yq 11 was previously known. In order to determine the exact size of the KAL interval, products of digestion of genomic DNA with EcoRI and HindIII obtained from patients LIL 155 and AM were also probed with the EcoRI fragments of the inserts in the λ phage. The most distal probe detecting the breakpoint from patient LIL 155 was located at about 10 kb at the distal end of the CRI-S232 locus.

The smallest detectable restriction fragments in the Xp 22.3; Yq 11 translocation for patient AM proved to be a HindIII fragment specific for the X chromosome of 2.3 kb and its homologous fragment specific for the Y chromosome of 2.8 kb.

From the distance between this X-specific fragment and the locus detected by the probe CRI-S232, the inventors deduced that the KAL interval had a length of about 67 kb. In addition, they obtained a more precise map of the breakpoint of the X chromosome inside this 2.3 kb HindIII fragment.

III) Search for the open reading frames in the KAL interval

DNAs from 7 overlapping recombinant λ phages (1-35, 2-38, 2-20, 2-33, 2-35, 1-16, proximal EcoRI fragment of 2–7), completely covering the KAL interval were sequenced. A single contig map of 67 kb was obtained and the complete sequence was analysed by computer methods in order to discriminate between the introns and the exons.

The computer program used was respectively based on codon preference (Staden and MacLachlan, 1982 (24)) and on a multi-criteria procedure. These analyses revealed a total of 19 putative exons, with different associated probabilities. Putative coding exons were searched out using known computer programs.

Figure 4:
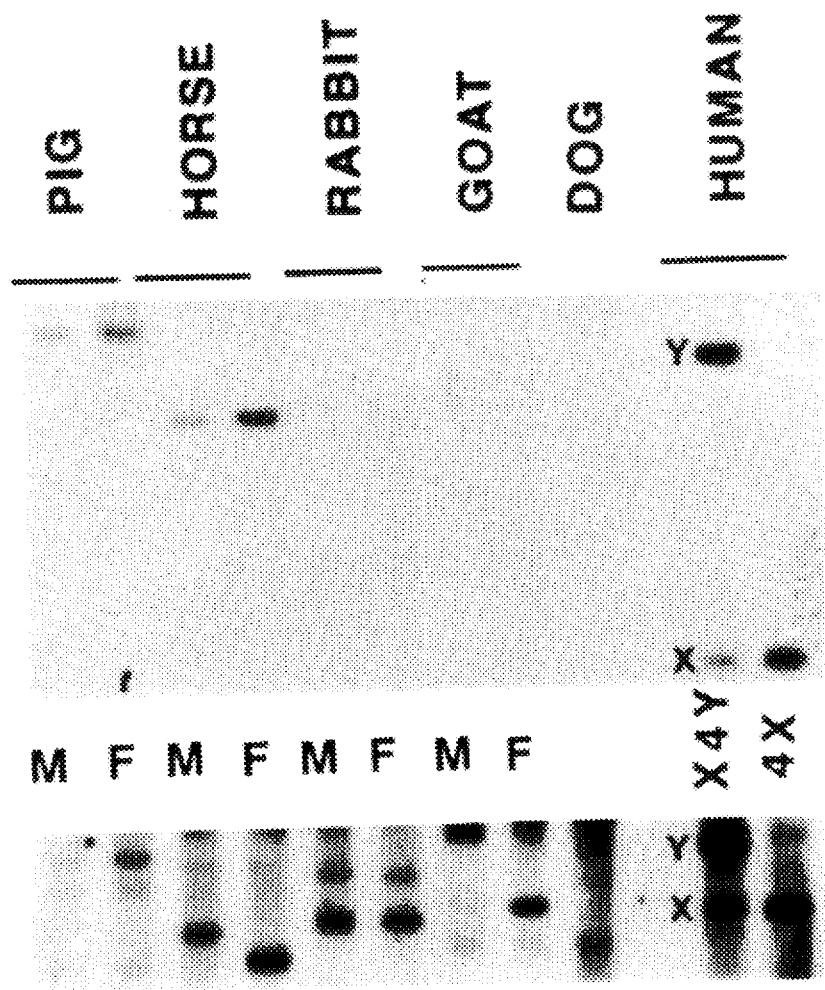
FIG. 4 represents the results of "zoo-blots" showing the sequences conserved among various animal species.

The sequences corresponding to each of these putative exons were amplified using the PCR technique and used as probes on "zoo-blots". The results of hybridization are represented in FIG. 4, where M represents the DNA from a male representative; F that from a female representative, for each species, the sex of the dog being non-determined).

Only two probes (485 S1 and CS1) made it possible to detect fragments of unique DNA in other mammalian species.

The sequence 485 S1 showed a sharp band in horses and pigs.

The sequence CS1 revealed a more complex hybridization pattern, comprising very strong bands (some of which are probably polymorphic) in certain species.

The probes 485 S1 and CS1 had given the best probability scores using the computer programs mentioned above. The sequence CS1 had been retained, in addition, partly because of a similiarity with N-CAM L1 (Cunningham et al., 1987 (11), Moss et al. 1988 (16)). Both sequences had the same transcriptional orientation.

IV) Screening of human cDNA libraries with the probe 485 S1 and isolation of a clone containing the ADMIX gene A cDNA library was generated from a macaccus fascicularis foetus at the 36th day of gestation, corresponding to the first day on which the expression of GnRH cells was observed in this species.

This library as well as the two human foetal brain cDNA libraries (H point) were screened with the probe 485 S1. Seven independent clones out of one million were isolated from the non-amplified macaque library and 5 to 7 clones from the other libraries.

The first sequences obtained from human clones had suggested that some cDNAs were either incompletely spliced insofar as they were interrupted by non-coding or chimeric sequences because one end hybridized with autosomes.

The sequencing of at least 3 independent coherent clones was performed for the coding part of the transcription product whereas the non-coding 3' part was defined from the sequencing of the corresponding genomic DNA.

Figure 5:
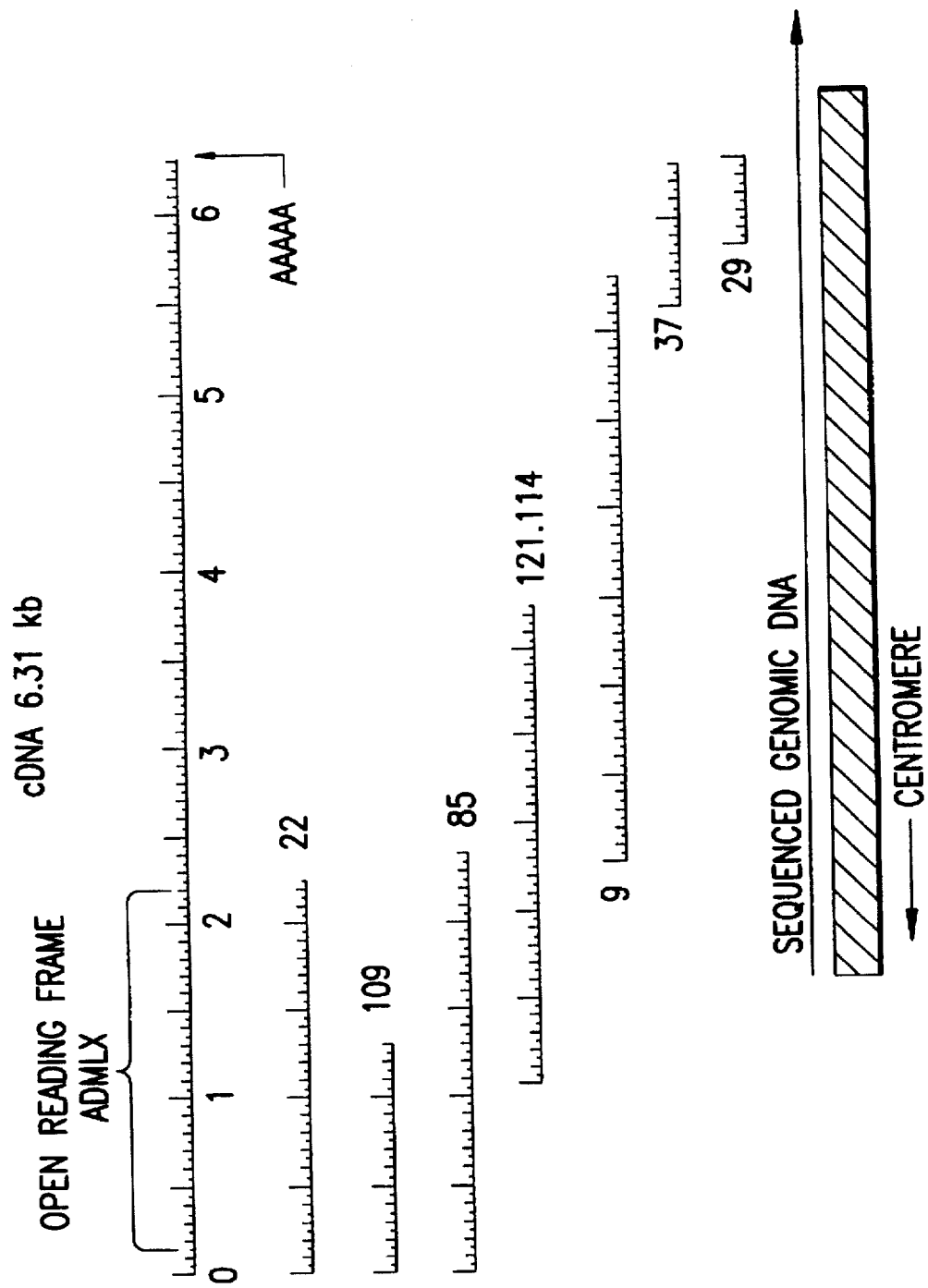
FIG. 5 represents the location of the ADMLX gene.

FIG. 5 represents the location of the ADMLX gene. Seven clones (22, 109, 85, 121, 114, 9, 37 and 29) were used for assembling the complete cDNA. Clones 22 and 85 contain the entire coding region. The terminal fragment of 4715 bases of the 3' end of the cDNA is contained in the proximal fragment of 8.1 kb of the KAL genomic DNA interval.

FIG. 6 represents the complete sequence of 6314 bases of the cDNA, which sequence is obtained from partially overlapping cDNA clones, and the corresponding peptide sequence.

The cDNA contains a long unique open reading frame (ADMLX) of 680 amino acids, starting at the first ATG codon, 151 nucleotides downstream of the 5' end of the cDNA.

This ATG initiation codon follows the eucaryotic consensus sequence Cc (A/G) CC ATG G (Kozak, 1986 (14)).

The untranslated 3' region is of an unusual size (4124 nucleotides) and is situated at a distance of 2.8 kb from a high polymorphic dinucleotide repeat; it contains 8 potential polyadenylation signals (AAUAAA). From the alignment with the available genomic sequence, the present inventors defined the last four exons.

The last four exons (4715 nucleotides) were mapped on a genomic DNA region of 8.1 kb.

The last exon of 4180 bp encodes only 19 amino acids.

Exon <1772-1992> corresponds to the probe 485 S1 and exon <1993-2134> is identical to the exon predicted for CS1.

Thus, the ADMLX gene contains the two exons which were revealed by analysis of the nucleotide sequence of the KAL interval.

The 5' end of the cDNA and the beginning of the coding region contain a group of dinucleotides CpG: one NotI site (position 580), one BssHII site (position 285) and 13 HpaII sites are counted in the first 580 nucleotides.

The amino acid sequence (in 1-letter IUPAC code) which is obtained by translation from the base sequence begins with a leader peptide which is presumed to be of the sequence MVPGVPGAVLTLCLWLAASSG (amino acid residues 1-21 SEQ ID NO:2).

Other parts define the domain rich in cysteine residues (<22-120>), the domain of the whey acidic protein type (WAP) (<134-176>), the centre of unit 1 of the twitchin type (<259-271>), the centre of the interval similar to N-CAM L1 (<624-654>).

The limits of the exons are indicated by T in FIG. 6.

V) Characterization of the ADMLX protein a) Analysis of the sequence

The predicted peptide sequence starts with a stretch of hydrophobic uncharged residues, which are characteristic tic of a signal peptide.

The cleavage of the latter (at the site predicted according to the method of Von Heijne, 1986 (27)) exposes cysteine 22 at the N-terminal end of the mature protein containing 659 amino acids and having a molecular weight, determined by calculation, of 74280. The binding of the glycosidic side chains to the potential glycosylation sites associated with the asparagine residues could confer a higher molecular mass on the protein.

The rest of the amino acid sequence corresponds to a relatively hydrophobic basic polypeptide (pI=9.72), not exhibiting a transmembrane domain.

The average tendency of forming α helices is low, the folding of the protein being predominantly of the β type.

The distribution of the cysteine residues in the sequence suggests the general organization of the ADMLX protein.

The 155 N-terminal amino acids of the mature polypeptide contain 19 cysteines whereas only 5 other cysteine residues are found in the next 504 residues.

The cysteine-rich region can, in addition, be divided into two separate clusters: a clear consensus WAP type core motif spanning the <134-176> segment and a different 12-cysteine cluster spanning the <22-120> region.

A final characteristic of the open reading frame of the ADMLX gene consists in a hydrophobic C-terminal region containing 10 basic residues histidine, lysine and arginine grouped into the 19 residues encoded by the last exon.

b) Search for homologies

The polypeptide chain between residues 181 and 661 exhibits numerous and significant similarities with the fibronectin type III repeat and with sequences related to this repeat.

By using the BLAST P program (Altschul, 1991 (2)) it was shown that the molecules exhibiting the greatest similarities with this region were rat fibronectin, the C. elegans twitchin, the human leucocytes common antigen related protein, and the chicken contactin/F11 and the human proteins N-CAM and L1.

VI) Expression of the ADMLX gene

A Northern blot hybridization of poly A(+) RNA from Macaccus fascicularis foetus (used for the cDNA library), from adult human brain cells and from NT2/D1 teratoma cells with a coding cDNA probe of 2 kb did not allow any transcription product to be detected.

The expression of the ADMLX gene was then studied by reverse transcription starting with RNA obtained from a variety of cell and tissue types followed by a PCR amplification by means of primers obtained from the cDNA sequence.

Three sets of primers placed along the coding region of the cDNA sequence (between positions 252 and 547, 1213 and 1533, 1713 and 2003) were used to analyse the expression of the gene.

These primers belonged to six different exons.

Amplification products were thus detected in all the tissues studied: adult brain, liver, kidney, skeletal muscle, lymphoblastoid cells and NT2/DA teratoma cells, foetal kidney and muscle.

The amplification products have the expected size and hybridize with the oligonucleotide probes of the invention.

VII) Characterization of a genetic abnormality in patients having an X chromosome-linked Kallmann syndrome Analysis of the sequence of exons V and VI by the PCR technique using the 2 pairs of primers SEQ ID No. 13 and SEQ ID No. 14 on the one hand, and SEQ ID No. 15 and SEQ ID No. 16 on the other hand, made it possible to detect nonsense mutations in 3 unrelated individuals suffering from a familial form of the disease. This proves that the ADMLX gene is the KAL gene responsible for the X chromosome-linked Kallmann syndrome (32).

REFERENCES

1—Albertsen, H. M., Abderrahim, H., Cann, H. M., Dausset, J. Lespalier, D., and Cohen, D. (1990). Construction and characterization of a yeast artificial chromosome library containing seven haploid human genome equivalents. Proc. Natl. Acad. Sci. U.S.A. 87, 4256–4260.

2—Altschul, S. F. (1991). Amino acid substitution matrices from an information theoric perspective. J. Mol. Biol. 219, 555–565.

3—Altschul, S. F., Gish, W. Miller, W., MLyers, E. W. and Lipman, D. J. (1990). Basic local alignment search tool. J. Mol. Biol. 215, 403–410.

4—Altschul, S. F., and Lipman, D. J. (1990). Protein database searches for multiple alignments. Proc. Natl. Acad. Sci. U.S.A. 87, 5509–5513.

5—Bairoch, A. (1991). PROSITE: A dictionary of sites and patterns in proteins. Nucl. Acids Res. 19, 2241–2245.

6—Ballabio, A., Bardoni, B., Guioli, S., Basler, E. and Camerino, G. (1990). Two families of low-copy number repeats are interspersed on Xp22.3: implications for the high frequency of deletions in this region. Genomics 8, 263–270.

7—Ballabio, A., Sebastion, G., Carrozzo, R., Parenti, G. Piccirillo. A., Persico, M. G. and Andria, G. (1987). Deletions of the steroid sulfatase gene in classical X-linked ichtyosis and in X-linked ichtyosis associated with Kallmann syndrome. Hum. Genet. 77, 338–341.

8—Bellané-Chantelot, C., Barillot, E., Lacroix, B., Lespalier, D., and Cohen, D. (1991). A test case for physical mapping of human genome by repetitive sequence fingerprints: construction of a physical map of 420 kb YAC subcloned into cosmids. Nucl. Acids Res. 19, 505–510.

9—Boguski, M., Ostell, J., and States, D. J. (1991). Molecular sequence databases and their uses. Protein engineering: a practical approach (Rees, A. R. Wetzel, R., and Sternberg, M. J. E. eds). IRL press 5. In press.

10—Claverie, J. M., Sauvaget, I. and Bougueleret, L. (1990). k-tuple frequency analysis: from intron/exon discrimination to T-cell epitope mapping. Meth. Enzymol. 183, 237–252.

11—Cunningham, B. A., Hempherly, J. J., Murray, B. A., Prediger, E. A., Brackenbury, R., and Edelman, G. M. (1987). Neural cell adhesion molecule: structure, immunoglobulin-like domains, cell surface modulation, and alternative RNA splicing. Science 236, 799–806.

12—Howley, P. M., Israel, M. A., Law, M. and Martin, M. A. (1979). A rapid method for detecting and mapping homology between heterologous DNAs. J. Biol. Chem. 254, 4876–4883.

13—Knowlton, R. G., Nelson, C. A., Brown, V. A., page D. C., and Donis-Keller, H. (1989). An extremely polymorphic locus on the short arm of the human X chromosome with homology to the long arm of the Y chromosome. Nucl. Acids Res. 17, 423–437.

14—Kozak, M. (1986). Point mutations define a sequence flanking the AUg initiator codon that modulates translation by eukaryotic ribosomes. Cell 44, 283–292.

15—Lipman, D. J., and Pearson, W. R. (1985). Rapid and sensitive protein similarity searches. Science 227, 1435–1441.

16—Moos, M. Tacke, R. Scherer, H., Teplow, D., Fruh, K., and Schachner, M. (1988). Neural adhesion molecule LI as a member of the immunoglobulin superfamily with binding domains similar to fibronectin. Nature 334, 701–703.

17—Nelson, D. L. Ledbetter, S. A., Corbo, L., Victoria, M. F., Ramirez-Solis, R. Webster, T. D., Ledbetter, D. H., and Caskey, C. T. (1989). Alu polymerase chain reaction: a method for rapid isolation of human-specific sequences from complex DNA sources. Proc. Natl. Acad. Sci. U.S.A. 86, 6686–6690.

18—Nelson, D. L., Ballabio, A., Victoria, M. F., Pieretti, M. Bies, R. D., Gibbs, R. A., Malley, J. A., Chinault, A. C. Webster, T. D., and Caskey, C. T. (1991). Alu-primed polymerase chain reaction for regional assignment of 110 yeast artificial chromosome clones from the human X chromosome: identification of clones associated with a disease locus. Proc. Natl. Acad. Sci. U.S.A. 88, 6157–6161.

19—Petit, C., Levilliers, J., and Weissenbach, J. (1988). Physical mapping of the human pseudo-autosomal region; comparison with genetic linkage map. EMBO J. 7, 2369–2376.

20—Petit, C., Levilliers, J., and Weissenbach, J. (1990a). Long-range restriction map of the terminal part of the short arm of the human X chromosome. proc. Natl. Acad. Sci. U.S.A. 87, 3680–3684.

21—Sambrook, J., Fritsch, E. F., and Maniatis, T. (1989). Molecular cloning. A laboratory manual (2nd edition). In Cold Spring Harbor University press, Cold Spring Harbor.

22—Schuler, G. D., Altschul, S. F., and Lipman, D. J. (1991). A workbench for multiple alignment construction and analysis. Proteins 9, 180–190.

23—Schwanzel-Fukuda, M., Bick, D., and Pfaff, D. W. (1989). Luteinizing hormone-releasing hormone (LHRH) expressing cells do not migrate normally in an inherited hypogonadal (Kallmann) syndrome. Mol. Brain Res. 6, 311–326.

24—Staden, R., and MacLachlan, A. D. (1982). Codon preference and its use in identifying protein coding regions in long DNA sequences. Nucl. Acids Res. 10, 141–156.

25—Staden, R. (1987). Computer handling of DNA sequencing projects. In nucleic acid and protein sequence analysis: a practical approach. Bishop, M. T., Rawlings, C. J., eds, IRL press, Oxford), pp. 173–217.

26—Tiepolo, L., Zuffardi, O. Fraccaro, M., di Natale, D., Gargantini, L., Müller, C. R., and Ropers, H. H. (1980). Assignment by deletion mapping of the steroid sulphatase X-linked ichtyosis locus to Xp223. Hum. Genet. 54, 205–206.

27—Von Heijne, G. (1986). A new method for predicting signal sequence cleavage sites. Nucl. Acids res. 14, 4683–4690.

28—Matthews, J. A. and Kricka, L. J., Anal. Biochem., 1988, 169, 1–25.

29—Orita M., Suzuki Y., Sekiya T., and Hayashi K. (1989). Rapid and Sensitive detection of point mutations and DNA polymorphisms using the polymerase chain reaction. Genomics 5, 874–879.

30—Myers, R. M., Sumelsky, N., Lerman, L. S., and Maniatis, T. (1985). Detection of single base substitutions in total genomic DNA. Nature (London) 313, 495–498.

31—Griffai et coll. Nucleic Acids Res. 1991, 19, 3887–3891.

32—Hardelin, J. -P. et al. (1992) X chromosome-linked Kallmann syndrome: Stop mutations validate the candidate gene. Proc. Natl. Acad. Sci. USA 89, 8190–8194.

| AMINO ACID SYMBOLS | | |
|---|---|---|
| A | Ala | alanine |
| C | Cys | cysteine |
| D | Asp | aspartic acid |
| E | Glu | glutamic acid |
| F | Phe | phenylalanine |
| G | Gly | glycine |
| H | His | histidine |
| I | Ile | isoleucine |
| K | Lys | lysine |
| L | Leu | leucine |
| M | Met | methionine |
| N | Asn | asparagine |
| P | Pro | proline |
| Q | Gln | glutamine |
| R | Arg | arginine |
| S | Ser | serine |
| T | Thr | threonine |
| V | Val | valine |
| W | Trp | tryptophan |
| Y | Tyr | tyrosine |

We claim:

1. An isolated nucleic acid fragment which is:
   (A) the nucleic acid sequence of SEQ ID NO: 1,
   (B) the nucleic acid sequence complementary to the nucleic acid sequence of SEQ ID NO:1,
   (C) a nucleic acid sequence encoding the amino acid sequence of SEQ ID NO:2,
   (D) a nucleic acid sequence complementary to a nucleic acid encoding the amino acid sequence of SEQ ID NO:2, or
   (E) a probe comprising at least 20 consecutive nucleotides of said nucleic acid sequence (A), (B), (C) or (D).

2. A cloning vector comprising said nucleic acid fragment according to claim 1.

3. An isolated nucleic acid probe specific for the gene associated with the X-chromosome-linked Kallmann syndrome, comprising at least 20 consecutive nucleotides from any one of nucleic acid sequences (A), (B), (C), (D) or (E) according to claim 1.

4. A plasmid p85B deposited at the Collection Nationale de Cultures de Microorganismes on 26 Sep. 1991 under Accession No. I-1146.

5. A pair of nucleic acid primers which can be used to specifically amplify the gene of SEQ ID NO:1 or fragments thereof.

6. A pair of nucleic acid primers according to claim 5, wherein said primers have a length of 18 to 30 nucleotides.

7. A pair of nucleic acid primers according to claim 6, wherein said primers have a length of 18 to 22 nucleotides.

8. A pair of nucleic acid primers which are of the sequences:

SEQ ID No. 3 and SEQ ID No. 4
SEQ ID No. 5 and SEQ ID No. 6
SEQ ID No. 7 and SEQ ID No. 8
SEQ ID No. 9 and SEQ ID No. 10
SEQ ID No. 11 and SEQ ID No. 12
SEQ ID No. 17 and SEQ ID No. 18
SEQ ID No. 19 and SEQ ID No. 20
SEQ ID No. 21 and SEQ ID No. 22
SEQ ID No. 23 and SEQ ID No. 24
SEQ ID No. 25 and SEQ ID No. 26
SEQ ID No. 27 and SEQ ID No. 28
SEQ ID No. 29 and SEQ ID No. 30, or
SEQ ID No. 31 and SEQ ID No. 32.

9. A method for detecting a genetic abnormality linked to the Kallmann syndrome in a biological sample containing human DNA comprising the following steps:
   a) bringing the biological sample containing the DNA into contact with a pair of specific primers according to one of claims 6, 8 or 5, under conditions permitting a hybridization of the primers with the human DNA contained in the biological sample;
   b) producing an amplification product by carrying out polymerase chain reaction;
   c) detecting the amplification products; and
   d) detecting a mutation or a deletion in the amplification products.

10. The method according to claim 9, wherein, in step d), a mutation is detected by the technique of single-strand conformation polymorphism (SSCP) analysis or by denaturing gradient gel electrophoresis (DGGE).

11. The method according to claim 9, wherein, in step d), a deletion is detected by determination of the length of the amplified fragments.

12. A kit for the detection of a genetic abnormality linked to the Kallmann syndrome in a biological sample, comprising the following elements:

a pair of specific primers according to one of claims 6, 8 or 5, and a standard comprising a nucleic acid fragment which is:
   (A) the nucleic acid sequence of SEQ ID NO: 1,
   (B) the nucleic acid sequence complementary to the nucleic acid sequence of SEQ ID NO:1,
   (C) a nucleic acid sequence encoding the amino acid sequence of SEQ ID NO:2,
   (D) a nucleic acid sequence complementary to a nucleic acid encoding the amino acid sequence of SEQ ID NO:2, or
   (E) a probe comprising at least 20 consecutive nucleotides of said nucleic acid sequence (A), (B), (C) or (D).

13. A peptide sequence comprising the amino acid of SEQ ID NO:2.

14. A peptide sequence a selected from the group consisting of:
   (A) the peptide sequence SEQ ID NO:2,
   (B) the peptide sequence between $C_{22}$ and $Y_{680}$ of the sequence SEQ ID NO:2,
   (C) fragments of the sequences (A) or (B), wherein said fragments bind to monoclonal antibodies capable of specifically detecting the peptide sequence SEQ ID NO:2, and
   (D) the peptide sequences which differ from the sequences (A), (B) or (C) by insertion, deletion or substitution of one or more amino acids, wherein said peptide sequences bind to monoclonal antibodies capable of specifically detecting the peptide sequence SEQ ID NO:2.

15. Monoclonal antibodies capable of specifically detecting a protein or a peptide having a peptide sequence according to claim 14.

16. A process for assaying a protein having a peptide sequence according to claim 14, comprising reacting monoclonal antibodies capable of specifically detecting said peptide sequence with said peptide sequence and detecting binding of said monoclonal antibodies to said peptide sequence.

* * * * *

SEQUENCE LISTING ( 1 ) GENERAL INFORMATION:

( i i i ) NUMBER OF SEQUENCES: 32

( 2 ) INFORMATION FOR SEQ ID NO: 1:

( i ) SEQUENCE CHARACTERISTICS:
( A ) LENGTH: 6314 base pairs

-continued ( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
( A ) ORGANISM: Homo sapiens
( H ) CELL LINE: foetal brain cells ( x i ) SEQUENCE DESCRIPTION: SEQ ID NO: 1:

| | | | | | | |
|---|---|---|---|---|---|---|
| GTCGGCGAGG | AGGGTCCGGC | CGGAGTTGAA | GGATTGAACT | TTCCGGCTCA | GTCGCGGCGG | 60 |
| CTGCCTGGTC | CTCAGCAGTG | CAGCCCCGGC | GCGGAGCAGG | GAGCCTCGGC | CCGCGCCCGG | 120 |
| CGCCCTCGCC | CTCGCCCTCG | ACCCGCAGCC | ATGGTGCCCG | GGTGCCCGG | CGCGGTCCTG | 180 |
| ACCCTCTGCC | TCTGGCTGGC | GGCCTCCAGC | GGCTGCCTGG | CGGCCGGCCC | CGGCGCGGCT | 240 |
| GCTGCGCGGC | GGCTGGACGA | GTCGCTGTCT | GCCGGGAGCG | TCCAGCGCGC | TCCGTGCGCC | 300 |
| TCCAGGTGCC | TGAGCCTGCA | GATCACTCGC | ATCTCCGCCT | TCTTCCAGCA | CTTCCAGAAC | 360 |
| AATGGTTCCC | TGGTTTGGTG | CCAGAATCAC | AAGCAATGTT | CTAAGTGCCT | GGAGCCCTGC | 420 |
| AAGGAATCAG | GGACCTGAG | GAAACACCAG | TGCCAAAGCT | TTTGTGAGCC | TCTCTTCCCC | 480 |
| AAGAAGAGCT | ACGAATGCTT | GACCAGCTGT | GAGTTCCTCA | AATACATCCT | GTTGGTGAAG | 540 |
| CAGGGGACT | GTCCGGCTCC | TGAGAAAGCC | AGTGGATTTG | CGGCCGCCTG | TGTTGAAAGC | 600 |
| TGCGAAGTTG | ACAATGAGTG | CTCTGGGGTG | AAGAAATGTT | GTTCGAATGG | GTGTGGACAC | 660 |
| ACCTGTCAAG | TACCCAAGAC | TCTGTACAAA | GGTGTCCCCC | TGAAGCCCAG | AAAAGAGTTA | 720 |
| CGATTTACAG | AACTGCAGTC | TGGACAGCTG | GAGGTTAAGT | GGTCCTCGAA | ATTCAATATT | 780 |
| TCTATTGAGC | CTGTGATCTA | TGTGGTACAA | AGAAGATGGA | ATTATGGAAT | CCATCCTAGC | 840 |
| GAAGATGACG | CCACTCACTG | GCAGACAGTG | GCCCAGACCA | CAGACGAGCG | AGTTCAACTG | 900 |
| ACTGACATAA | GACCCAGCCG | ATGGTACCAG | TTTCGAGTGG | CTGCTGTGAA | TGTGCATGGA | 960 |
| ACTCGAGGCT | TCACTGCCCC | CAGCAAACAC | TTCCGTTCTT | CCAAAGATCC | ATCTGCCCCA | 1020 |
| CCAGCACCGG | CTAACCTCCG | GCTGGCCAAC | TCCACCGTCA | ACAGTGATGG | GAGTGTGACC | 1080 |
| GTCACTATAG | TTTGGGATCT | CCCCGAGGAG | CCGGACATCC | CTGTGCATCA | TTACAAGGTC | 1140 |
| TTTTGGAGCT | GGATGGTCAG | CAGTAAGTCT | CTTGTCCCAA | CAAAGAAGAA | GCGGAGAAAG | 1200 |
| ACTACGGATG | GGTTTCAAAA | TTCTGTGATC | CTGGAGAAAC | TCCAGCCAGA | CTGTGACTAT | 1260 |
| GTTGTGGAAT | TGCAAGCCAT | AACGTACTGG | GGACAGACAC | GGCTGAAGAG | TGCAAAGGTG | 1320 |
| TCCCTTCACT | TCACATCGAC | ACATGCAACC | AACAACAAAG | AACAGCTTGT | GAAAACTAGA | 1380 |
| AAAGGTGGAA | TTCAAACACA | ACTCCCTTTT | CAAAGACGAC | GACCCACTCG | CCCGCTGGAA | 1440 |
| GTCGGAGCTC | CCTTCTATCA | GGATGGCCAA | CTGCAAGTTA | AAGTCTACTG | GAAGAAGACA | 1500 |
| GAAGATCCCA | CTGTCAACCG | ATATCATGTG | CGGTGGTTTC | CTGAAGCGTG | TGCCCACAAC | 1560 |
| AGAACAACCG | GATCAGAGGC | ATCATCTGGC | ATGACCCACG | AAAATTACAT | AATTCTTCAA | 1620 |
| GATCTGTCAT | TTTCCTGCAA | GTATAAGGTG | ACTGTCCAAC | CAATACGGCC | AAAAAGTCAC | 1680 |
| TCCAAGGCAG | AAGCTGTTTT | CTTCACTACT | CCACCATGCT | CTGCTCTTAA | GGGGAAGAGC | 1740 |
| CACAAGCCTA | TTGGCTGCCT | GGGCGAAGCA | GGTCATGTTC | TTTCTAAGGT | GCTAGCTAAG | 1800 |
| CCTGAGAACC | TTTCTGCTTC | ATTCATCGTC | CAGGATGTGA | ACATCACCGG | TCACTTTTCT | 1860 |
| TGGAAGATGG | CCAAGGCCAA | TCTCTATCAG | CCCATGACTG | GGTTTCAAGT | GACTTGGGCT | 1920 |

```
GAGGTCACTA CGGAAAGCAG ACAGAACAGC CTACCCAACA GCATTATTTC ACAGTCCCAG   1980
ATTCTGCCTT CCGATCATTA TGTCCTAACA GTGCCCAATC TGAGACCATC TACTCTTTAC   2040
CGACTGGAAG TGCAAGTGCT GACCCCAGGA GGGGAGGGGC CGGCCACCAT CAAGACGTTC   2100
CGGACGCCGG AGCTCCCACC CTCTTCAGCA CACAGATCTC ATCTTAAGCA TCGTCATCCA   2160
CATCATTACA AGCCTTCTCC AGAAAGATAC TAAACTGTTC AAAAAGATTT TGTGAAATTG   2220
CACAGATGTG TAAGCTTGTT GAACTTCGGC CACGAGACAT GCACACTTCC AGAGGCAGTG   2280
GGAACTGCTC AGAGGCCCGG ACTCTCCTAT GTGACTTTAG TGCAGGAAGA ACTTCTGTCA   2340
ATCATGGACG CATCTGGAGA CAAGTGAGAA ACAGTAGATT GGTGAAGACA GACACCAGTT   2400
CCCTACAAGC ATGGAGAAAA TGAAGAATAG GCCTGTTTAA TGCTAAATTT TGTTTTCATG   2460
TATGGTGTCG CTCATTTCTA TTGAATTACA ACAGAACTCA GTTTCCCTG  AATTGGAGC    2520
ACCAAACTCC GCCCCAAAAA GGAGAGTAAC AAATACACAA TTCACACATA ACACTAAGCG   2580
TAAATCTAAT CAATAAAATA TATTTTGAC  TAAATTATTG ATTCGATATG AAAAATCAAC   2640
TAAGATTACA CAGCTTTGTT TTTTGAATC  TTTCCTAAGA TCATTTTTAT CCTAGGTGAT   2700
TTTTAAATGA AAATGTGTAA TCTAAAATAT ACCAGCGAAT TTAAATCTAA AAATGCTCCT   2760
ACTTTAAGTA CCTTGTGCTG CTCTTTATGC AAAGGTAAAT CAAAGTTCCC TCTATAAATT   2820
ATGATTTACA AAAGACACCC AAGCCAGAGG AACTCAATGA AATAAGCTGC TAATCAGATT   2880
TTACCTTGGA GAAATGAAAA TTATTTCTTG GGGATGCCTT TAATATTTG  ATCCTATTAT   2940
GTGAGAGATT TTCCTGATAT GTTATCTTAT TTATATTTTC CCTTATTTTC CTCAATGCAG   3000
ATAATAGCTT TTGGTGCACT TTTGTTTCAC CATCTGAAAA TTCACAAAAC TTCTTGCTTC   3060
AAATGAAAAA ATCCCAACTA TTGAGCATGT TTAAATCTTT GCAGAGATTT GCCTTTTCTT   3120
AATCAAAGAA AGGTCTTTGT GTGCTAGAAT ATTATTGGTA ATGTTTTAAA AATTCCTTTG   3180
ATTGATAGAG AAGGACAGTT ATTTGCATTT AATTCACCCA TATGCTTTCA AATCTAGTAT   3240
ATCTTACTTT TTGGAAATGT TTATGCTAC  AAATTAGTGC CTTGTAGCAT GAACTTAAGT   3300
CAAAACGTGT TATCAATATA GAGTGTTGCA GTGTATATTG TAACAACCTA AAACGCAGAG   3360
AAGTTTAATT TAATACTGTT TTTTTTCTTG AAGGAATACT CACATACATG GTTTGAAATG   3420
TGCATAGATA TGCATGTCTA TATAATTATA AATGCATGTG TATATATATG CAAATATATG   3480
TACATATACA TGTATATACA CACAGACACA TGCATATACA TGAATATACC TTGAGCATGA   3540
ATCCCTGGAG AAATCGTTTT CGTAGGCTCA CCAATGGTGA GTAAAGATAC AGCTCTTTTA   3600
AAGGTCATAA GGATAATATA TTTTCCCCAT CAATGCTGAT TCTGAGAAAA GAGCAATTTA   3660
TCAAAATTAA ACACTGTAAA AGAAAGGTGT CCATATGTCT TTACCTACCT AAGTAAAACA   3720
GGAAGAAAAT CAGTAACATT ATCCTTAGGT TTGACAATG  GTACTTGCTT CTTGTTGTTT   3780
TATTGTTTCC TGAATTCATG CAGATGCCTG GCCATTCCTG GAAGAGTGG  ATAACTCAGA   3840
AGTCACTGTA CTCCACAGAG CCTCACTGCA GTGTCTAAAG GTAGATGCAA ATTAAAATGC   3900
AGGGAAAATA ACTTTTCTGA TGTTGATGCA TGTCTTTGGG AAACACATTT ATAAACATGG   3960
ATACCTGATA ATAGATATTG AAACCCATTT CCTGTGTGTT AAAATATTTA AAAGTGGAT   4020
ATTCCAGGAA TGTTTTGCAG CTTTGTACAA GTAACATAAA TTGGACACCT CAGAATGAAA   4080
GTTCATGTTG GTTCTGAATG GTTCACTGCA GCTCCTGTCA CAAGCTGGGA TGGATTTATC   4140
ACATTGAGTT ATGAAATTAC CTGGTTCTAA GAATTTTTGA GTGGCAAAAA TAGAAAACAA   4200
TCTTCATTTG AAAACATCCC TAAGCTTGAA TAAATGGATA CCATAGATAG CTTCTCTTTT   4260
TTATTCTGGT GTCATTACCA GCATCTGAAT TTCAAGTTCT TAAAATTTCA AAAATTAAAA   4320
```

-continued

```
TTTTTCATTA  TTAGCTATCC  ATTTATCTTT  TACATGAACT  TGTCATGAAC  AAATTCAAAT   4380
GTTATGCCA   GCAAATTTTT  GTACTGTTGC  ATAGTTAAAA  ATGCTGGGAG  TCTCTGCATA   4440
GATACAAAAT  ATTATTAAAT  TATTACATAA  ATTTAATTTT  ATAAAATTTA  ATCATGCTTC   4500
TTTTGTCTGG  TAATAGACAT  TGGACAGATA  TTTTTAGTTC  AGATGGTGAT  TCTGAAGCTT   4560
ACATCTCCCT  TAAAAAAATC  TAAAGCAGCT  CTTATGGGCT  TCTAATTTTA  ATATAAATAA   4620
ATAATTTAAA  TTTTATTGGT  GTTATTGGAA  GAAAAATGCT  ATTAATGGGC  TAATAAAAAA   4680
CATGTGTTTC  TCTTATGGAT  TTTAATAAGC  TCCAGTATTA  TTCAAATGAT  CAAAAATATA   4740
GTTATAATTT  TTTGAATTTT  AAAAATGTGA  TTGCTCTAAT  AAAGAATAAA  ATCTATGCTT   4800
TTTAACAAAC  ATAGTTTTGG  TGCCTAATTC  TGTAATATGT  TTTATTGAAA  TTAGATTCAT   4860
TTCTCTAATG  TGAGAAAAAT  ATATCCAGTA  ATAGTATTGA  CTGTTAAAA   AATTGAGCTC   4920
ATCAAAAATA  TTGTCATCAA  ATACAGGTGG  TTAATCTGAC  ATACATTGCA  GTTACATGCA   4980
TTATTTTTAT  TTACAACATT  TGCTCCTTAA  TGATGAATTT  ATCTGTGTTA  CCCTGTTTTT   5040
CTACCTGGAA  CTCCATAGAA  TGATGTTTGC  AAACCAACAT  GTGCTCTTTT  CAGTCATTCA   5100
CTGTTTTAAT  ATGACATGGT  AGAGAAGATA  AGGTTTATGG  CAGGTAATTT  TTTGTAATGT   5160
GTATTAAACG  AAGTTCAAAG  ATTAGAAATA  CATCTGTGTC  CTGAAAACCT  TAGATACATA   5220
GCCGACTGTA  TACAGAGGTT  CATCTCAACC  TCAACACTAT  TGACTTTTGG  GGCTGGATAG   5280
TTCTCTGTTG  TGGGGGTTTG  TCTTGTGCAC  TGTAGGTTTT  TAGTAGCATC  CACACTTTCT   5340
CCTCACCAGA  TGCCAGTTGC  ACCCTCCCCC  AAGTTGAGAC  AACCAAAAAT  GTCTCCAGAT   5400
ATTGCCAGCT  ACCCCTTGAG  GGATGGTACC  TCTGGTTGAG  AACCATTGCT  AGAGAATGAT   5460
CTTTACTGAA  TTTGCCCTTT  ATAAGAAACC  CAGTGAATTT  CTAGAGCAAG  TCCCAAAAAC   5520
TAAGGGACAG  CTAAGAAGTT  ATTATGGTTG  ACTTCAAAGG  CCTAAACTGT  GTTTTTATG    5580
TCCACTAAAC  AACTTGATTA  AAAGACGGAA  TTTTGACTCG  TGTCTGTATC  ATACAAGTAC   5640
AAATACTAAT  TTTGCCCTAT  GTATCCGTAA  ATGTCATTTG  TGATTTGAC   TTATTTATT    5700
AATGCCCTTT  CTTATGCCGT  GGGTTTTCAA  GTTACTCAT   TTCTATGGTT  GCAAATAACT   5760
CTAAAACTTA  TTATATAAAC  TTTCATATTA  TAGGCAGAAC  ACAATGGCTA  AATATCTGTT   5820
GCATGTACTT  TAAAGTTTAT  TATAAAATAT  AAACAGATAT  ATAAAGATGT  TGACTCTTAC   5880
CTGTGATTTT  GCATGGTCAG  ACTCGGTGTC  AGGTACGGAG  AGGATTCTCA  TGACTGTCTT   5940
ACCTCTACTG  AATATTCTAG  TGAGTTATAT  GATTACGGA   GTGATTAACA  GAGGTCTATA   6000
TAAAGTTACT  TTTCCCCTTT  ACTTAATTAT  ATTGTAGTGT  GCAGATAACA  AAACTGCTAC   6060
CTTCTCATCC  AAGTGGTCTG  TAGAATTCAT  GTCCCTTACA  GTGGTCATTT  AAAGTCAATA   6120
TTTATTTATG  TATGTAATAA  AAAAGTTGG   ATTTTGTGT   ATGTCTGTCA  CATTATTTAG   6180
AGAGAAGTAA  TCTTGTAAAA  ATGTTTTGTA  AAAACAAAA   AAGTATTGTA  AATAGTCTTG   6240
ATATTCTGTG  ACTCATTATT  TTCATGTTAG  AGTTTGTACA  TACTGGTTCA  ATAATAAAGT   6300
ATCCTTAAAC  CAGA                                                        6314
```

( 2 ) INFORMATION FOR SEQ ID NO: 2:

( i ) SEQUENCE CHARACTERISTICS:
        ( A ) LENGTH: 680 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i i i ) ANTI-SENSE: NO ( v i ) ORIGINAL SOURCE:
    ( A ) ORGANISM: Homo sapiens
    ( H ) CELL LINE: foetal brain cell ( x i ) SEQUENCE DESCRIPTION: SEQ ID NO: 2:

```
Met Val Pro Gly Val Pro Gly Ala Val Leu Thr Leu Cys Leu Trp Leu
 1               5                  10                       15

Ala Ala Ser Ser Gly Cys Leu Ala Ala Gly Pro Gly Ala Ala Ala Ala
             20              25                  30

Arg Arg Leu Asp Glu Ser Leu Ser Ala Gly Ser Val Gln Arg Ala Pro
         35                  40                  45

Cys Ala Ser Arg Cys Leu Ser Leu Gln Ile Thr Arg Ile Ser Ala Phe
     50                  55                  60

Phe Gln His Phe Gln Asn Asn Gly Ser Leu Val Trp Cys Gln Asn His
 65              70                  75                       80

Lys Gln Cys Ser Lys Cys Leu Glu Pro Cys Lys Glu Ser Gly Asp Leu
             85                  90                  95

Arg Lys His Gln Cys Gln Ser Phe Cys Glu Pro Leu Phe Pro Lys Lys
             100                 105                 110

Ser Tyr Glu Cys Leu Thr Ser Cys Glu Phe Leu Lys Tyr Ile Leu Leu
         115                 120                 125

Val Lys Gln Gly Asp Cys Pro Ala Pro Glu Lys Ala Ser Gly Phe Ala
     130                 135                 140

Ala Ala Cys Val Glu Ser Cys Glu Val Asp Asn Glu Cys Ser Gly Val
145                 150                 155                 160

Lys Lys Cys Cys Ser Asn Gly Cys Gly His Thr Cys Gln Val Pro Lys
                 165                 170                 175

Thr Leu Tyr Lys Gly Val Pro Leu Lys Pro Arg Lys Glu Leu Arg Phe
             180                 185                 190

Thr Glu Leu Gln Ser Gly Gln Leu Glu Val Lys Trp Ser Ser Lys Phe
         195                 200                 205

Asn Ile Ser Ile Glu Pro Val Ile Tyr Val Val Gln Arg Arg Trp Asn
210                 215                 220

Tyr Gly Ile His Pro Ser Glu Asp Asp Ala Thr His Trp Gln Thr Val
225                 230                 235                 240

Ala Gln Thr Thr Asp Glu Arg Val Gln Leu Thr Asp Ile Arg Pro Ser
                 245                 250                 255

Arg Trp Tyr Gln Phe Arg Val Ala Ala Val Asn Val His Gly Thr Arg
             260                 265                 270

Gly Phe Thr Ala Pro Ser Lys His Phe Arg Ser Ser Lys Asp Pro Ser
         275                 280                 285

Ala Pro Pro Ala Pro Ala Asn Leu Arg Leu Ala Asn Ser Thr Val Asn
     290                 295                 300

Ser Asp Gly Ser Val Thr Val Thr Ile Val Trp Asp Leu Pro Glu Glu
305                 310                 315                 320

Pro Asp Ile Pro Val His His Tyr Lys Val Phe Trp Ser Trp Met Val
                 325                 330                 335

Ser Ser Lys Ser Leu Val Pro Thr Lys Lys Lys Arg Arg Lys Thr Thr
             340                 345                 350

Asp Gly Phe Gln Asn Ser Val Ile Leu Glu Lys Leu Gln Pro Asp Cys
         355                 360                 365

Asp Tyr Val Val Glu Leu Gln Ala Ile Thr Tyr Trp Gly Gln Thr Arg
     370                 375                 380
```

| | | | | | | | | | | | | | |
|---|---|---|---|---|---|---|---|---|---|---|---|---|---|
| Leu 385 | Lys | Ser | Ala | Lys 390 | Val | Ser | Leu | His | Phe 395 | Thr | Ser | Thr | His | Ala | Thr 400 |
| Asn | Asn | Lys | Glu | Gln 405 | Leu | Val | Lys | Thr | Arg 410 | Lys | Gly | Gly | Ile | Gln 415 | Thr |
| Gln | Leu | Pro | Phe 420 | Gln | Arg | Arg | Arg | Pro 425 | Thr | Arg | Pro | Leu | Glu 430 | Val | Gly |
| Ala | Pro | Phe 435 | Tyr | Gln | Asp | Gly | Gln 440 | Leu | Gln | Val | Lys | Val 445 | Tyr | Trp | Lys |
| Lys | Thr 450 | Glu | Asp | Pro | Thr | Val 455 | Asn | Arg | Tyr | His | Val 460 | Arg | Trp | Phe | Pro |
| Glu 465 | Ala | Cys | Ala | His | Asn 470 | Arg | Thr | Thr | Gly | Ser 475 | Glu | Ala | Ser | Ser | Gly 480 |
| Met | Thr | His | Glu | Asn 485 | Tyr | Ile | Ile | Leu | Gln 490 | Asp | Leu | Ser | Phe | Ser 495 | Cys |
| Lys | Tyr | Lys | Val 500 | Thr | Val | Gln | Pro | Ile 505 | Arg | Pro | Lys | Ser | His 510 | Ser | Lys |
| Ala | Glu | Ala | Val 515 | Phe | Phe | Thr | Thr 520 | Pro | Pro | Cys | Ser | Ala 525 | Leu | Lys | Gly |
| Lys | Ser 530 | His | Lys | Pro | Ile | Gly 535 | Cys | Leu | Gly | Glu | Ala 540 | Gly | His | Val | Leu |
| Ser 545 | Lys | Val | Leu | Ala | Lys 550 | Pro | Glu | Asn | Leu | Ser 555 | Ala | Ser | Phe | Ile | Val 560 |
| Gln | Asp | Val | Asn | Ile 565 | Thr | Gly | His | Phe | Ser 570 | Trp | Lys | Met | Ala | Lys 575 | Ala |
| Asn | Leu | Tyr | Gln 580 | Pro | Met | Thr | Gly 585 | Phe | Gln | Val | Thr | Trp 590 | Ala | Glu | Val |
| Thr | Thr | Glu 595 | Ser | Arg | Gln | Asn | Ser 600 | Leu | Pro | Asn | Ser | Ile 605 | Ile | Ser | Gln |
| Ser | Gln 610 | Ile | Leu | Pro | Ser | Asp 615 | His | Tyr | Val | Leu | Thr 620 | Val | Pro | Asn | Leu |
| Arg 625 | Pro | Ser | Thr | Leu | Tyr 630 | Arg | Leu | Glu | Val | Gln 635 | Val | Leu | Thr | Pro | Gly 640 |
| Gly | Glu | Gly | Pro | Ala 645 | Thr | Ile | Lys | Thr | Phe 650 | Arg | Thr | Pro | Glu | Leu 655 | Pro |
| Pro | Ser | Ser | Ala 660 | His | Arg | Ser | His | Leu 665 | Lys | His | Arg | His | Pro 670 | His | His |
| Tyr | Lys | Pro 675 | Ser | Pro | Glu | Arg | Tyr 680 | | | | | | | | |

( 2 ) INFORMATION FOR SEQ ID NO: 3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Homo sapiens ( x i ) SEQUENCE DESCRIPTION: SEQ ID NO: 3:

CAGCCAATGG TGCGGCCTCC TGTCC        25

( 2 ) INFORMATION FOR SEQ ID NO: 4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Homo sapiens ( x i ) SEQUENCE DESCRIPTION: SEQ ID NO: 4:

TCCCGGCAGA CAGCGACTCG T     21

( 2 ) INFORMATION FOR SEQ ID NO: 5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Homo sapiens ( x i ) SEQUENCE DESCRIPTION: SEQ ID NO: 5:

CCTCGCCCTC GCCCTCGACC CGCAG     25

( 2 ) INFORMATION FOR SEQ ID NO: 6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Homo sapiens ( x i ) SEQUENCE DESCRIPTION: SEQ ID NO: 6:

GAACTTTGCG AGCCCAGGCT GGGAG     25

( 2 ) INFORMATION FOR SEQ ID NO: 7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
                ( A ) ORGANISM: Homo sapiens ( x i ) SEQUENCE DESCRIPTION: SEQ ID NO: 7:

TTGGAAGGGA AGGACAGCAG G                                                                                  2 1

( 2 ) INFORMATION FOR SEQ ID NO: 8:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
                ( A ) ORGANISM: Homo sapiens ( x i ) SEQUENCE DESCRIPTION: SEQ ID NO: 8:

GCACCATTCA TACAGGTATA G                                                                                  2 1

( 2 ) INFORMATION FOR SEQ ID NO: 9:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
                ( A ) ORGANISM: Homo sapiens ( x i ) SEQUENCE DESCRIPTION: SEQ ID NO: 9:

TCTCAGCTTT GTTTGTTTCC A                                                                                  2 1

( 2 ) INFORMATION FOR SEQ ID NO: 10:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
                ( A ) ORGANISM: Homo sapiens ( x i ) SEQUENCE DESCRIPTION: SEQ ID NO: 10:

CGTAAGCATA GTCAGATTTG G                                                                                  2 1

( 2 ) INFORMATION FOR SEQ ID NO: 11:

( i ) SEQUENCE CHARACTERISTICS:
                ( A ) LENGTH: 21 base pairs
                ( B ) TYPE: nucleic acid (C) STRANDEDNESS: single
                    (D) TOPOLOGY: linear (ii) MOLECULE TYPE: cDNA (iii) HYPOTHETICAL: NO (iii) ANTI-SENSE: NO (vi) ORIGINAL SOURCE:
                    (A) ORGANISM: Homo sapiens (xi) SEQUENCE DESCRIPTION: SEQ ID NO: 11:

ATGTCTTGGA AATCAGACTT C                                                                    21

(2) INFORMATION FOR SEQ ID NO: 12:

(i) SEQUENCE CHARACTERISTICS:
                    (A) LENGTH: 21 base pairs
                    (B) TYPE: nucleic acid
                    (C) STRANDEDNESS: single
                    (D) TOPOLOGY: linear (ii) MOLECULE TYPE: cDNA (iii) HYPOTHETICAL: NO (iii) ANTI-SENSE: NO (vi) ORIGINAL SOURCE:
                    (A) ORGANISM: Homo sapiens (xi) SEQUENCE DESCRIPTION: SEQ ID NO: 12:

ATGTGACACT GCATGTGTCT T                                                                    21

(2) INFORMATION FOR SEQ ID NO: 13:

(i) SEQUENCE CHARACTERISTICS:
                    (A) LENGTH: 21 base pairs
                    (B) TYPE: nucleic acid
                    (C) STRANDEDNESS: single
                    (D) TOPOLOGY: linear (ii) MOLECULE TYPE: cDNA (iii) HYPOTHETICAL: NO (iii) ANTI-SENSE: NO (vi) ORIGINAL SOURCE:
                    (A) ORGANISM: Homo sapiens (xi) SEQUENCE DESCRIPTION: SEQ ID NO: 13:

CAGATTGTTT TAATTGATAC G                                                                    21

(2) INFORMATION FOR SEQ ID NO: 14:

(i) SEQUENCE CHARACTERISTICS:
                    (A) LENGTH: 21 base pairs
                    (B) TYPE: nucleic acid
                    (C) STRANDEDNESS: single
                    (D) TOPOLOGY: linear (ii) MOLECULE TYPE: cDNA (iii) HYPOTHETICAL: NO (iii) ANTI-SENSE: NO (vi) ORIGINAL SOURCE:
                    (A) ORGANISM: Homo sapiens (xi) SEQUENCE DESCRIPTION: SEQ ID NO: 14:

GCAGACACTA CCTCCAGGAT G                                                                  21

( 2 ) INFORMATION FOR SEQ ID NO: 15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Homo sapiens ( x i ) SEQUENCE DESCRIPTION: SEQ ID NO: 15:

AGTGACATGT TCCCTGTGCT C                                                                  21

( 2 ) INFORMATION FOR SEQ ID NO: 16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Homo sapiens ( x i ) SEQUENCE DESCRIPTION: SEQ ID NO: 16:

CTGGTAGCAA GGATAGTATT C                                                                  21

( 2 ) INFORMATION FOR SEQ ID NO: 17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Homo sapiens ( x i ) SEQUENCE DESCRIPTION: SEQ ID NO: 17:

ATGATGTGTC TTTGTACTGG G                                                                  21

( 2 ) INFORMATION FOR SEQ ID NO: 18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO (i i i) ANTI-SENSE: NO (v i) ORIGINAL SOURCE:
    (A) ORGANISM: Homo sapiens (x i) SEQUENCE DESCRIPTION: SEQ ID NO: 18:

TGGGAATAAC AATCCTTCCT C                                       21

(2) INFORMATION FOR SEQ ID NO: 19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i i i) ANTI-SENSE: NO (v i) ORIGINAL SOURCE:
        (A) ORGANISM: Homo sapiens (x i) SEQUENCE DESCRIPTION: SEQ ID NO: 19:

GACGTGGAAG GTTTGTAACG C                                       21

(2) INFORMATION FOR SEQ ID NO: 20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i i i) ANTI-SENSE: NO (v i) ORIGINAL SOURCE:
        (A) ORGANISM: Homo sapiens (x i) SEQUENCE DESCRIPTION: SEQ ID NO: 20:

ATCATGTCAC AATCATCTTG A                                       21

(2) INFORMATION FOR SEQ ID NO: 21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i i i) ANTI-SENSE: NO (v i) ORIGINAL SOURCE:
        (A) ORGANISM: Homo sapiens (x i) SEQUENCE DESCRIPTION: SEQ ID NO: 21:

TGCCCAGGAA TCTATAATTA C                                       21

(2) INFORMATION FOR SEQ ID NO: 22:

(i) SEQUENCE CHARACTERISTICS:

( A ) LENGTH: 21 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
( A ) ORGANISM: Homo sapiens ( x i ) SEQUENCE DESCRIPTION: SEQ ID NO: 22:

ACTATCTCTA TATTACTGTG C        21

( 2 ) INFORMATION FOR SEQ ID NO: 23:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
( A ) ORGANISM: Homo sapiens ( x i ) SEQUENCE DESCRIPTION: SEQ ID NO: 23:

ACCTGGAATG TAACATCCAG C        21

( 2 ) INFORMATION FOR SEQ ID NO: 24:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
( A ) ORGANISM: Homo sapiens ( x i ) SEQUENCE DESCRIPTION: SEQ ID NO: 24:

ACCATTCTGC TTTCCACTTC C        21

( 2 ) INFORMATION FOR SEQ ID NO: 25:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
( A ) ORGANISM: Homo sapiens ( x i ) SEQUENCE DESCRIPTION: SEQ ID NO: 25:

AATATGATTT CAATTCTTGC C                                    21

( 2 ) INFORMATION FOR SEQ ID NO: 26:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Homo sapiens ( x i ) SEQUENCE DESCRIPTION: SEQ ID NO: 26:

GATGTAGAAG TCCTTCAGGT G                                    21

( 2 ) INFORMATION FOR SEQ ID NO: 27:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Homo sapiens ( x i ) SEQUENCE DESCRIPTION: SEQ ID NO: 27:

TCTCCAGTCG CCTAATCCTG G                                    21

( 2 ) INFORMATION FOR SEQ ID NO: 28:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Homo sapiens ( x i ) SEQUENCE DESCRIPTION: SEQ ID NO: 28:

CCAATGACAC AGACATAGTA C                                    21

( 2 ) INFORMATION FOR SEQ ID NO: 29:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA -continued (iii) HYPOTHETICAL: NO (iii) ANTI-SENSE: NO (vi) ORIGINAL SOURCE:
    (A) ORGANISM: Homo sapiens (xi) SEQUENCE DESCRIPTION: SEQ ID NO: 29:

GTGCATTGCA TGTTGTCTCT G    21

(2) INFORMATION FOR SEQ ID NO: 30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: Homo sapiens (xi) SEQUENCE DESCRIPTION: SEQ ID NO: 30:

TGACAGGATG GCTTAATGCC C    21

(2) INFORMATION FOR SEQ ID NO: 31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: Homo sapiens (xi) SEQUENCE DESCRIPTION: SEQ ID NO: 31:

ATGTTACTGA CATATTTTGT C    21

(2) INFORMATION FOR SEQ ID NO: 32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: Homo sapiens (xi) SEQUENCE DESCRIPTION: SEQ ID NO: 32:

GGCCGAAGTT CAACAAGCTT A    21